United States Patent
Carrara et al.

(10) Patent No.: US 7,335,379 B2
(45) Date of Patent: *Feb. 26, 2008

(54) TRANSDERMAL PHARMACEUTICAL FORMULATION FOR MINIMIZING SKIN RESIDUES

(75) Inventors: R. Dario Norberto Carrara, Oberwil (CH); Arnaud Grenier, Steinbrunn le Haut (FR); Celine Besse, Saint Louis (FR)

(73) Assignee: Antares Pharma IPL AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/371,042

(22) Filed: Mar. 7, 2006

(65) Prior Publication Data

US 2006/0153905 A1    Jul. 13, 2006

Related U.S. Application Data

(63) Continuation of application No. PCT/EP2004/011175, filed on Oct. 6, 2004.

(60) Provisional application No. 60/510,613, filed on Oct. 10, 2003.

(51) Int. Cl.
  *A61F 13/00* (2006.01)
(52) U.S. Cl. ..................................... 424/449
(58) Field of Classification Search ................ 424/400, 424/449; 514/946, 947
See application file for complete search history.

(56) References Cited

U.S. PATENT DOCUMENTS

| | | | |
|---|---|---|---|
| 4,597,961 A | 7/1986 | Etscorn | 424/28 |
| 4,704,406 A | 11/1987 | Stanislaus et al. | 514/570 |
| 4,832,953 A | 5/1989 | Campbell et al. | 424/448 |
| 4,973,468 A * | 11/1990 | Chiang et al. | 424/449 |
| 5,053,227 A | 10/1991 | Chiang et al. | 424/448 |
| 5,059,426 A | 10/1991 | Chiang et al. | 424/449 |
| 5,230,896 A | 7/1993 | Yeh et al. | 424/443 |
| 5,278,176 A | 1/1994 | Lin | 514/343 |
| 5,352,457 A * | 10/1994 | Jenkins | 424/448 |

(Continued)

FOREIGN PATENT DOCUMENTS

EP    1325 752 A2    7/2003

(Continued)

OTHER PUBLICATIONS

Ralph Lipp et al., XP-002121357, "Selection And Use Of Crystallization Inhibitors For Matrix-Type Transdermal Drug-Delivery Systems Containing Sex Steroids", Journal of Pharm. Pharmacol, vol. 50, pp. 1343-1349 (1998).

(Continued)

*Primary Examiner*—Johann Richter
*Assistant Examiner*—Konata M. George
(74) *Attorney, Agent, or Firm*—Winston & Strawn LLP

(57) ABSTRACT

This invention relates to novel transdermal or transmucosal pharmaceutical formulation which reduces the occurrences of contamination of other individuals and the transference to clothing of the user. The novel formulation includes at least one pharmacologically active ingredient, and a solvent system having a monoalkylether of diethylene glycol and a glycol present in specified ratios, and a mixture of water and alcohol. The invention also relates to a method for inhibiting or delaying crystallization of an active agent in a pharmaceutical formulation.

45 Claims, 14 Drawing Sheets

Diffusion Chamber

U.S. PATENT DOCUMENTS

| | | | | |
|---|---|---|---|---|
| 5,580,574 | A * | 12/1996 | Behl et al. | 424/449 |
| 5,603,947 | A | 2/1997 | Wong et al. | 424/448 |
| 5,633,008 | A | 5/1997 | Osborne et al. | 424/448 |
| 5,658,587 | A | 8/1997 | Santus et al. | 424/448 |
| 5,662,890 | A | 9/1997 | Punto et al. | 424/59 |
| 5,783,207 | A | 7/1998 | Stanley et al. | 424/440 |
| 5,891,462 | A | 4/1999 | Carrara | 424/449 |
| 5,932,243 | A | 8/1999 | Fricker et al. | 424/450 |
| 5,935,604 | A | 8/1999 | Illum | 424/501 |
| 6,034,079 | A | 3/2000 | Sanberg et al. | 514/225.8 |
| 6,165,497 | A | 12/2000 | Osborne et al. | 424/448 |
| 6,166,044 | A | 12/2000 | Samdborn et al. | 514/343 |
| 6,267,985 | B1 | 7/2001 | Chen et al. | 424/451 |
| 6,299,900 | B1 | 10/2001 | Reed et al. | 424/449 |
| 6,383,471 | B1 | 5/2002 | Chen et al. | 424/45 |
| 6,417,205 | B1 | 7/2002 | Cooke et al. | 514/343 |
| 6,426,078 | B1 | 7/2002 | Bauer et al. | 424/401 |
| 6,465,005 | B1 | 10/2002 | Biali et al. | 424/449 |
| 6,479,076 | B2 | 11/2002 | Blank | 424/484 |
| 6,596,740 | B2 | 7/2003 | Jones | 514/343 |
| 6,828,336 | B2 | 12/2004 | Walling | 514/343 |
| 6,911,475 | B1 | 6/2005 | Cesaro et al. | 514/567 |
| 6,995,265 | B2 | 2/2006 | Comins et al. | 546/14 |
| 7,029,692 | B1 | 4/2006 | Bracht | 424/449 |
| 2003/0199426 | A1 * | 10/2003 | Carrara et al. | 514/2 |
| 2004/0198706 | A1 * | 10/2004 | Carrara et al. | 514/169 |
| 2004/0219197 | A1 * | 11/2004 | Carrara et al. | 424/449 |

FOREIGN PATENT DOCUMENTS

| | | |
|---|---|---|
| WO | WO 95/18603 | 7/1995 |
| WO | WO 95/29678 | 11/1995 |

OTHER PUBLICATIONS

Pramila N. Kotiyana et al., "Eudragits: Role As Crystallization Inhibitors In Drug-In-Adhesive Transdermal Systems Of Estradiol", European Journal of Pharmaceutics and Biopharmaceutics, vol. 52 pp. 173-180 (2001).

Katrin Moser et al., "Passive Skin Penetration Enhancement And Its Quantification In Vitro", European Journal of Pharmaceutics and Biopharmaceutics, vol. 52, pp. 103-112 (2001).

P. Mura et al., XP-002315954, "Evaluation Of Transcutol As A Clonazepam Transdermal Permeation Enhancer From Hydrophilic Gel Formulations", European Journal of Pharmaceutical Sciences, vol. 9, pp. 365-372 (2000).

* cited by examiner

Diffusion Chamber

In-Vitro 24-Hour Biodistribution of Testosterone

24-Hour Biodistribution of Minoxidil

In-Vitro Permeation of Testosterone

24-Hour Biodistribution of Testosterone

A
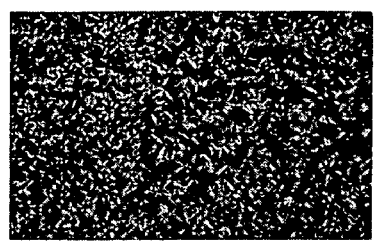
B
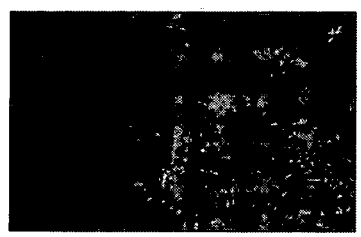
C
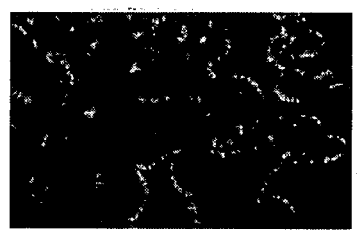
D
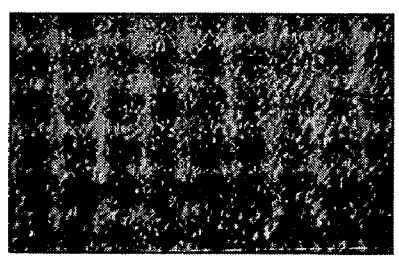
E
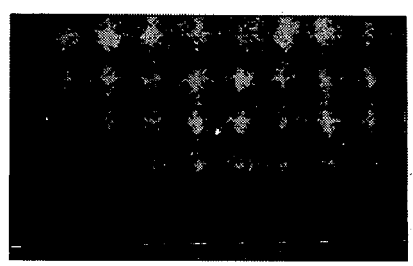
F
G
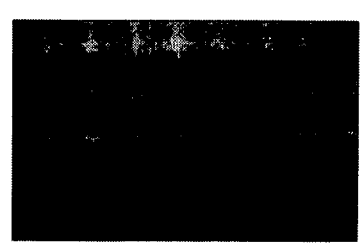
H
Figures 6A - 6H  Comparative Crystallization Kinetic Studies Comparative Drug Flux Profile For Selegiline Formulations Comparative Kinetic Profile of In-Vitro Permeation of Selegilline Formulations Comparative Kinetic Profile of In-Vitro Permeation of Fentanyl Formulations Comparative Drug Flux Profile of Fentanyl Formulations Comparative Kinetic Profile of In-Vitro Permeation of Fentanyl Formulations Comparative Drug Flux Profile of Fentanyl Formulations Comparative Kinetic Profile of In-Vitro Permeation of Buspirone Formulations Comparative Drug Flux Profile of Buspirone Formulations

TRANSDERMAL PHARMACEUTICAL FORMULATION FOR MINIMIZING SKIN RESIDUES

CROSS REFERENCE

This application is a continuation of International application PCT/EP2004/011175 filed Oct. 6, 2004 and claims the benefit of U.S. Provisional Application No. 60/510,613, filed Oct. 10, 2003, the content of each of which is expressly incorporated herein by reference.

FIELD OF INVENTION

The present invention relates to a novel transdermal or transmucosal pharmaceutical formulation comprising an active ingredient and a solvent system. The solvent system includes a monoalkyl ether, and glycol in specific ratios, as well as mixture of alcohol and water. The invention also relates to a method of delaying or inhibiting crystallization of an active agent in a transdermal or transmucosal pharmaceutical formulation.

BACKGROUND OF THE INVENTION

It is known that transdermal or transmucosal dosage forms conveniently deliver drugs across a localized area of the skin or the mucosa. One such way of delivering drugs across the skin or mucosa is by way of a non-occlusive transdermal and/or topical dosage form. Some non-limiting examples of non-occlusive transdermal and topical semi-solid dosage forms include creams, ointments, gels, foams, sprays, solutions, and lotions (i.e. emulsions, or suspensions). Typically non-occlusive dosage forms are applied to the skin or mucosa and are left uncovered and open in the atmosphere. Because the non-occlusive dosage form is left uncovered, unwanted transfer of the pharmaceutical formulation to the clothing of the user or even to other individuals in close proximity to the user is unavoidable. Other drawbacks of the non-occlusive dosage form include evaporation of the formulation, removal of the formulation from the skin or mucosa, for example, by bathing or by other activities, and the inabsorption of the formulation through the skin, which is discussed below.

The inefficiencies of drug permeation across or through the skin or mucosa barriers are known. It is also known that the permeation of a drug in a non-occlusive transdermal or transmucosal dosage form can be as little as 1% and usually is no more than 15%. Thus, a vast majority of the active drug remains unabsorbed on the skin or mucosa surface. Because the vast majority of the drug remains on the skin and does not penetrate the skin or mucosa surfaces, the bioavailability of the particular drug is not optimal, and also a high risk of contamination of other individuals in close proximity to the user is presented by the unwanted transfer of the pharmaceutical formulation in the non-occlusive dosage form.

Problems associated with the unwanted transfer of a particular pharmaceutical formulation to others are well documented. For example, Delanoe et al. reported the androgenization of female partners of volunteers applying a testosterone gel preparation during contraceptive studies. (Delanoe, D., Fougeyrollas, B., Meyer, L. & Thonneau, P. (1984): "*Androgenisation of female partners of men on medroxyprogesterone acetate/percutaneous testosterone contraception*", Lancet 1, 276-277). Similarly, Yu et al. reported virilization of a two-year-old boy after incidental and unintentional dermal exposure to a testosterone cream applied to his father's arm and back (Yu, Y. M., Punyasavatsu, N., Elder, D. & D'Ercole, A. J. (1999): "*Sexual development in a two-year old boy induced by topical exposure to testosterone*", Pediatrics, 104, 23).

Moreover, the patient information brochure for ANDROGEL® (1% testosterone gel from Unimed Pharmaceuticals Inc.) emphasizes the potential for transfer of testosterone to other people and/or clothing and the brochure includes safety measures to be taken by the individual using the non-occlusive dosage form.

One way to overcome or minimize this contamination issue is to physically protect the transdermal dosage form by covering skin with the applied pharmaceutical formulation means of a patch device, a fixed reservoir, an application chamber, a tape, a bandage, a sticking plaster, or the like, which remain on the skin at the site of application of the formulation for a prolonged length of time. This is usually accomplished with occlusive dosage forms.

Occlusive dosage forms present some advantages over non-occlusive dosage forms such as assisting the rate of penetration of drugs across the skin by maintaining the thermodynamic activity of the drug close to its maximum (the thermodynamic activity of a drug in a dermal formulation is proportional to the concentration of the drug and the selection of the vehicle, and according to the laws of thermodynamics, the maximum activity of a drug is related to that of the pure drug crystal). However occlusive dosage forms also exhibit several major drawbacks. For example, occlusive dosage forms present a high potential of local skin irritation caused by the prolonged contact on the skin of the drug, volatiles, vehicle excipients, and the adhesive used to attach the occlusive device, e.g., the patch, to the skin. In addition, the occlusive nature of certain occlusive dosage forms, such as the patch device, also restrict the natural ability of the skin to "breathe," and thereby increases the risk of irritation.

In addition to the aforementioned drawbacks of occlusive dosage forms, significant serious hazards have been documented regarding the high drug loading that is specific to patches. For example, several cases of abuses with remaining fentanyl in fentanyl patches have been reported. See, Marquardt K. A., Tharratt R. S., "Inhalation abuse of fentanyl patch.", J Toxicol Clin. Toxicol. 1994; 32(1):75-8; Marquardt K. A., Tharratt R. S., Musallam N. A., "Fentanyl remaining in a transdermal system following three days of continuous use.", Ann Pharmacother. 1995 October; 29(10): 969-71; Flannagan L M, Butts J D, Anderson W H., "Fentanyl patches left on dead bodies—potential source of drug for abusers.", J Forensic Sci. 1996 March; 41(2):320-1. Severe incidental intoxication cases have also been documented. See Hardwick Jr., W, King, W., Palmisano, P., "Respiratory Depression in a Child Unintentionally Exposed to Transdermal Fentanyl Patch", Southern Medical Journal, September 1997.

Patch products typically contain patient information, which clearly indicate the risks discussed above. For instance, OXYTROL™ (an oxybutynin patch commercialized by WATSON Pharmaceuticals, Inc. USA) contains patient information that indicates the following warning: "Since the patch will still contain some oxybutynin, throw it away so that it can not be accidentally worn or swallowed by another person, especially a child." The high level of active drug residues is thus a critical drawback of patches. Such accidents could not occur with the use of gel formulations.

Although attempts have been made to overcome drawbacks associated with both occlusive and non-occlusive drug forms, such attempts have been futile. For example, as noted above, one drawback of non-occlusive dosage forms is evaporation of the formulation, which is left open in the atmosphere. The formulation of non-occlusive supersaturated systems could have achieved an ideal merge but transdermal formulations, which rely on supersaturation technologies, present a major drawback of formulation instability, both prior to and during application to the skin due to solvent evaporation. Davis A F and Hadgraft J—Supersaturated solutions as topical drug delivery systems, Pharmaceutical Skin Penetration Enhancement, Marcel Dekker Inc, New York (1993) 243-267 ISBN 0 8247 9017 0, which is incorporated herein by reference.

Notably, extraordinary physicochemical changes occur with the evaporation of the solvent system, which result in modifications of the concentration of the active agent, which may even lead to drug precipitation, thereby altering the diffusional driving force of the formulation. See Ma et al, Proceed. Intern. Symp. Control. Rel. Bioact. Mater., 22 (1995). Consequently, the percutaneous absorption of the active agent may be quite different from that when the solvent was present.

In addition, controlling drug crystallization is of particular interest for non-occlusive transdermal systems. Campbell et al. resorted to a method of heating a crystalline hydrate to a temperature above the melting point in order to prevent the crystallization of the formulation. See, U.S. Pat. No. 4,832, 953. Ma et al found that PVP added to the matrix acts as an effective crystallization inhibitor for norethindrone acetate transdermal delivery systems. See, Int. J. of Pharm. 142 (1996) pp. 115-119). DE-A-4210711 affirms that cholesterol and $SiO_2$ are crystallization inhibitors for 17-.beta.-estradiol transdermal delivery system. WO 95/18603 describes soluble PVP as crystal inhibitor for patch devices and affirms that soluble PVP increases the solubility of a drug without negatively affecting the adhesivity or the rate of drug delivery from the pressure-sensitive adhesive composition.

Additionally, the inhibition of crystallization in transdermal devices was reported by Biali et al. See, U.S. Pat. No. 6,465,005 in which it is described that the use of a steroid (estradiol for instance) as an additive in a process of manufacture or storage of a transdermal device acts as a crystallization inhibitor during storage of the device.

Further, transdermal delivery from semi-solid formulations faces antinomic requirements. The drug delivery system should enable absorption of an extensive amount of active drug through the skin within the shortest period of time in order to prevent contamination of individuals, transfer to clothing or accidental removing. The drug delivery system should also provide sustained release of the active drug over 24 hours ideally, so that only once-daily application is required. This drug delivery system should also prevent drug crystallization at the application surface area.

Drug delivery systems having such properties may be achieved by combining various solvents. A volatile solvent may be defined as a solvent that changes readily from solid or liquid to a vapor, that evaporates readily at normal temperatures and pressures. Here below is presented data for some usual solvents, where volatility is reflected by the molar enthalpy of vaporization $\Delta_{vap}H$, defined as the enthalpy change in the conversion of one mole of liquid to gas at constant temperature. Values are given, when available, both at the normal boiling point $t_b$, referred to a pressure of 101.325 kPa (760 mmHg), and at 25° C. (From "Handbook of Chemistry and Physics, David R. Lide, 79$^{th}$ edition (1998-1999)—Enthalpy of vaporization (6-100 to 6-115). Stanislaus et al. (U.S. Pat. No. 4,704,406 on Oct. 9, 2001) defined as volatile solvent a solvent whose vapor pressure is above 35 mm Mg when the skin temperature is 32° C., and as non-volatile solvent a solvent whose vapor pressure is below 10 mm Mg at 32° C. skin temperature. Examples of non-volatile solvents include, but are not limited to, propylene glycol, glycerin, liquid polyethylene glycols, or polyoxyalkylene glycols. Examples of volatile solvents include, but are not limited to, ethanol, propanol, or isopropanol.

TABLE 1

Enthalpy of vaporization of certain solvents

| | $t_b$ | $\Delta_{vap}H$ ($t_b$) | $\Delta_{vap}H$ (25° C.) |
|---|---|---|---|
| Ethanol | 78.3 | 38.6 | 42.3 |
| Propan-2-ol (isopropanol) | 82.3 | 39.9 | 45.4 |
| Propanol | 97.2 | 41.4 | 47.5 |
| Butan-2-ol | 99.5 | 40.8 | 49.7 |
| Butan-1-ol | 117.7 | 43.3 | 52.4 |
| Ethylene glycol monomethyl ether | 124.1 | 37.5 | 45.2 |
| Ethylene glycol monoethyl ether | 135.0 | 39.2 | 48.2 |
| Ethylene glycol monopropyl ether | 149.8 | 41.4 | 52.1 |
| 1,2-Propylene glycol | 187.6 | 52.4 | Not available |
| Diethylene glycol monomethyl ether | 193.0 | 46.6 | Not available |
| Diethylene glycol monoethyl ether | 196.0 | 47.5 | Not available |
| 1,3-Propylene glycol | 214.4 | 57.9 | Not available |
| Glycerin | 290.0 | 61.0 | Not available |

Numerous authors have investigated evaporation and transdermal penetration from solvent systems. For Example, Spencer et al. (Thomas S. Spencer, "*Effect of volatile penetrants on in vitro skin permeability*", AAPS workshop held in Washington D.C. on Oct. 31-Nov. 1, 1986) established that the relationship between volatility and penetration is not absolute and depends on many parameters such as for instance hydration of the tissue or the solubility of the penetrant in the tissue. Stinchcomb et al. reported that the initial uptake of a chemical (hydrocortisone, flurbiprofen) from a volatile solvent system (acetone) is more rapid than that from a non-volatile solvent system (aqueous solution). With an aqueous solution, close to the saturation solubility of the chemical, the driving force for uptake remains more or less constant throughout the exposure period. Conversely, for a volatile vehicle which begins evaporating from the moment of application, the surface concentration of the chemical increases with time up to the point at which the solvent has disappeared; one is now left with a solid film of the chemical from which continued uptake into the stratum corneum may be very slow and dissolution-limited.

Risk assessment following dermal exposure to volatile vehicles should pay particular attention, therefore, to the duration of contact between the evaporating solvent and the skin (Audra L. Stinchcomb, Fabrice Pirot, Gilles D. Touraille, Annette L. Bunge, and Richard H. Guy, "*Chemical uptake into human stratum corneum in vivo from volatile and non-volatile solvents*", Pharmaceutical Research, Vol. 16, No 8, 1999). Kondo et al. studied bioavailability of percutaneous nifedipine in rats from binary (acetone and propylene glycol PG or isopropyl myristate IPM) or ternary (acetone-PG-IPM) solvent systems, compared with the results from simple PG or IPM solvent systems saturated with the drug. (Kondo et al. S, Yamanaka C, Sugimoto I., "*Enhancement of transdermal delivery by superfluous thermodynamic potential. III. Percutaneous absorption of nifedipine in rats*", J Pharmaco Biodyn. 1987 December; 10(12):743-9).

U.S. Pat. No. 6,299,900 to Reed et al. discloses a non-occlusive, percutaneous, or transdermal drug delivery system-having active agent, safe and approved sunscreen as penetration enhancer, and optional volatile liquid. The invention describes a transdermal drug delivery system, which comprises at least one physiologically active agent or prodrug thereof and at least one penetration enhancer of low toxicity being a safe skin-tolerant ester sunscreen. The composition comprises an effective amount of at least one physiologically active agent, at least one non-volatile dermal penetration enhancer; and at least one volatile liquid.

U.S. Pat. No. 5,891,462 to Carrara discloses a pharmaceutical formulation in the form of a gel suitable for the transdermal administration of an active agent of the class of estrogens or of progestin class or of a mixture of both, comprising lauryl alcohol, diethylene glycol monoethyl ether and propylene glycol as permeation enhancers.

Mura et al. describe the combination of diethylene glycol monoethyl ether and propylene glycol as a transdermal permeation enhancer composition for clonazepam (Mura P., Faucci M. T., Bramanti G., Corti P., "Evaluation of transcutol as a clonazepam transdermal permeation enhancer from hydrophilic gel formulations", Eur. J. Pharm. Sci., 2000 February; 9(4): 365-72)

Williams et al. reports the effects of diethylene glycol monoethyl ether (TRANSCUTOL™) in binary co-solvent systems with water on the permeation of a model lipophilic drug across human epidermal and silastic membranes (A. C. Williams, N. A. Megrab and B. W. Barry, "Permeation of oestradiol through human epidermal and silastic membranes from saturated TRANSCUTOL®/water systems", in Prediction of Percutaneous Penetration, Vol. 4B, 1996). Many references may also illustrate the effect of TRANSCUTOL™ as an intracutaneous drug depot builder well known to one skilled in the art.

U.S. Pat. No. 5,658,587 to Santus et al. discloses transdermal therapeutic systems for the delivery of alpha adrenoceptor blocking agents using a solvent enhancer system comprising diethylene glycol monoethyl ether and propylene glycol.

U.S. Pat. No. 5,662,890 to Punto et al. discloses an alcohol-free cosmetic compositions for artificially tanning the skin containing a combination of diethylene glycol monoethyl ether and dimethyl isosorbide as permeation enhancer.

U.S. Pat. No. 5,932,243 to Fricker et al. discloses a pharmaceutical emulsion or microemulsion preconcentrate for oral administration of macrolide containing a hydrophilic carrier medium consisting of diethylene glycol monoethyl ether, glycofurol, 1,2-propylene glycol, or mixtures thereof.

U.S. Pat. Nos. 6,267,985 and 6,383,471 to Chen et al. disclose pharmaceutical compositions and methods for improved solubilization of triglycerides and improved delivery of therapeutic agents containing diethylene glycol monoethyl ether and propylene glycol as solubilizers of ionizable hydrophobic therapeutic agents.

U.S. Pat. No. 6,426,078 to Bauer et al. discloses an oil-in water microemulsion containing diethylene glycol monoethyl ether or propylene glycol as co-emulsifier of lipophilic vitamins.

Many research experiments have been carried out on diethylene glycol monoethyl ether (marketed under the trademark TRANSCUTOL™ by Gattefossé) as an intracutaneous drug depot builder. For example, Ritschel, W. A., Panchagnula, R., Stemmer, K., Ashraf, M., "Development of an intracutaneous depot for drugs. Binding, drug accumulation and retention studies, and mechanism depot for drugs", Skin Pharmacol, 1991; 4: 235-245; Panchagnula, R. and Ritschel, W. A., "Development and evaluation of an intracutaneous depot formulation of corticosteroids using TRANSCUTOL® as a cosolvent, in vitro, ex vivo and in-vivo rat studies", J. Pharm. Pharmacology. 1991; 43: 609-614; Yazdanian, M. and Chen, E., "The effect of diethylene glycol monoethyl ether as a vehicle for topical delivery of ivermectin", Veternary Research Corn. 1995; 19: 309-319; Pavliv, L., Freebern, K., Wilke, T., Chiang, C-C., Shetty, B., Tyle, P., "Topical formulation development of a novel thymidylate synthase inhibitor for the treatment of psoriasis", Int. J. Pharm., 1994; 105: 227-233; Ritschel, W. A., Hussain, A. S., "In vitro skin permeation of griseofulvin in rat and human skin from an ointment dosage form", Arzneimeittelforsch/Drug Res. 1988; 38: 1630-1632; Touitou, E., Levi-Schaffer, F., Shaco-Ezra, N., Ben-Yossef, R. and Fabin, B., "Enhanced permeation of theophylline through the skin and its effect on fibroblast proliferation", Int. J. Pharm., 1991; 70: 159-166; Watkinson, A. C., Hadgraft, J. and Bye, A., "Enhanced permeation of prostaglandin $E_2$ through human skin in vitro", Int. j. Pharm., 1991; 74: 229-236; Rojas, J., Falson, F., Courraze, G., Francis, A., and Puisieux, F., "Optimization of binary and ternary solvent systems in the percutaneous absorption of morphine base", STP Pharma Sciences, 1991; 1: 71-75; Ritschel, W. A., Barkhaus, J K., "Use of absorption promoters to increase systemic absorption of coumarin from transdermal drug delivery systems", Arzneimeittelforsch/Drug Res. 1988; 38: 1774-1777.

Thus there remains a need to provide a pharmaceutically acceptable transdermal or transmucosal pharmaceutical formulation or drug delivery system that exhibits the advantages of both occlusive systems (high thermodynamic activity) and non-occlusive systems (low irritation and sensitization potential, and excellent skin tolerance) while overcoming the disadvantages of these systems. The novel transdermal or transmucosal pharmaceutical formulation of the present invention satisfies this need.

SUMMARY OF INVENTION

The transdermal or transmucosal pharmaceutical formulation of the present invention comprises at least one active agent; and a solvent system present in an amount sufficient to solubilize the at least one active ingredient and inhibit crystallization of the at least one active ingredient on a skin or mucosal surface of a mammal. Other advantages of the transdermal or transmucosal pharmaceutical formulation of the invention include reducing or preventing the transfer of the formulation to clothing or another, minimizing contamination of clothing by the formulation, modulation of biodistribution of the active agent within different layers of the skin and facilitation of absorption of the active agent by the skin or mucosa surface to name a few.

The novel solvent system of the present invention includes a monoalkyl ether, present in an amount of between about 1% and 30% by weight of the solvent system, a glycol, present in an amount of between about 1% and 30% by weight of the solvent system. The monoalkyl ether and glycol are present in a weight ratio of 10:1 to 2:1 or 1:2 to 1:10. The solvent system further includes a mixture of an alcohol and water. The mixture present in an amount of between about 40% and 98% of the solvent system, wherein the alcohol is present in an amount of about 5% to 80% of the mixture, and the water is present in an amount of about 20% to 95% of the mixture.

Surprisingly, it has been discovered that the combinative use of a monoalkyl ether of diethylene glycol and a glycol at specified ratios, preferably in hydro-alcoholic formulations, prevents or significantly reduces the transfer of active drug(s) from transdermal semi-solid formulations to clothing or other surfaces, significantly reduces the transfer to individuals; and also prevents or significantly reduces the loss of active drug(s)—and therefore the loss of therapeutic efficiency—consecutive to accidental removing due to daily activities such as washing, swimming or the like.

Other advantages of the present invention include the discovery that the association of a monoalkyl ether and a glycol at specified ratios exhibit a synergic effect and inhibits crystallization of the active ingredient(s) in transdermal semi-solid formulations. In addition, it has been discovered, against the background described above, a totally unexpected control of the active drug(s) distribution in the different layers of the skin is achieved when modifying the range of the monoalkyl ether:glycol ratio described in the present invention, simultaneously but independently from the crystallization inhibitor effect above mentioned.

Further, it has also been found that the glycol acts as a modulator of the capability of monoalkyl ether to build a drug depot in the different layers of the skin. Also, the significant reduction of unabsorbed active drug(s) remaining at the application surface area results from the simultaneous although independent inhibition of crystallization and transdermal drug penetration, enhanced or not by additional permeation enhancer(s).

BRIEF DESCRIPTION OF THE DRAWINGS

FIGS. 6A to 6H illustrate results of crystallization kinetic studies of prior art compositions compared to formulations in accordance with the present invention.

DETAILED DESCRIPTION OF THE PREFERRED EMBODIMENTS

Figure 1:
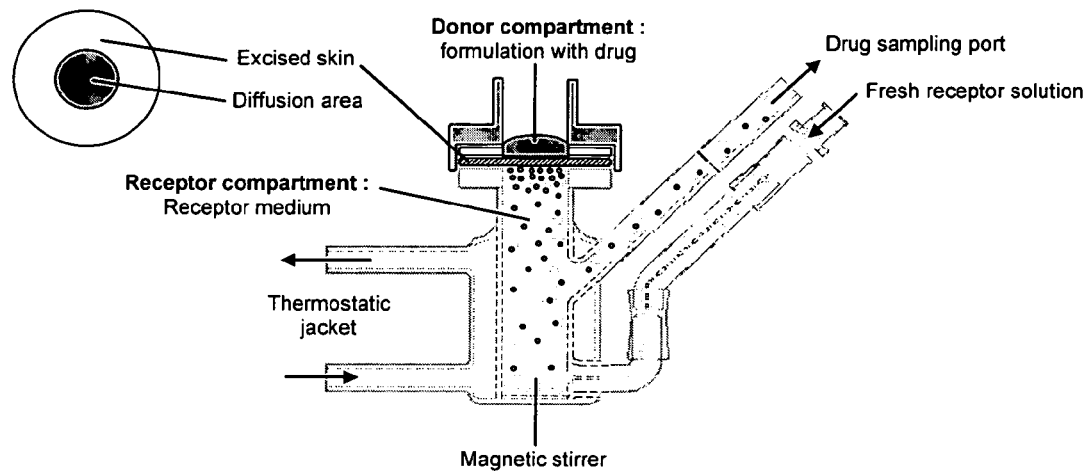
FIG. 1 is schematically illustrates a diffusion chamber used for vertical diffusion cell used for in vitro testing of oxybutynin transdermal formulations.

The present invention is directed to a novel transdermal or transmucosal pharmaceutical formulation. The formulation comprises at least one active ingredient and a solvent system. The solvent system including a monoalkyl ether, a glycol and a hydro-alcohol mixture. In accordance with the present invention, the transdermal or a transmucosal drug delivery formulation is in the form of a semi-solid formulation, gel, a cream, an ointment, a lotion (i.e. an emulsion or a dispersion), a solution, a foam, or a spray. Although alternatives are also in the scope of the claims.

The phrase "semi-solid" formulation means a heterogeneous system in which one solid phase is dispersed in a second liquid phase.

The phrase "transdermal" delivery, applicants intend to include both transdermal (or "percutaneous") and transmucosal administration, i.e., delivery by passage of a drug through the skin or mucosal tissue and into the bloodstream.

The phrase "pharmacologically active" or "physiologically active" to describe "ingredient" or "agent" as used herein means any chemical material or compound suitable for transdermal or transmucosal administration which induces a desired systemic effect.

The phrase "therapeutically effective" amount of a pharmacologically active agent means a non toxic but sufficient amount of a compound to provide the desired therapeutic effect.

The phrase "non-occlusive" system as used herein means a system that does not trap nor segregate the skin from the atmosphere by means of for instance a patch device, a fixed reservoir, an application chamber, a tape, a bandage, a sticking plaster, or the like which remains on the skin at the site of application for a prolonged period of time.

The phrase "contamination" or "transfer" as used herein means the unintended presence of harmful substances in individuals or surfaces by direct contact between individuals, between surfaces, or between individuals and surfaces (and reciprocally).

The phrase "synergy", "synergism", "synergistic effect" or "synergistic action" as used herein means an effect of the interaction of the actions of two agents such that the result of the combined action is greater than expected as a simple additive combination of the two agents acting separately.

The phrase "modulate", "regulate" or "control" as used herein means to adjust, or maintain, with respect to a desired rate, degree, or condition, as to adjust permeation rate, crystallization speed, repartition of an active pharmaceutical ingredient in the layers of the skin.

The phrase "effective" or "adequate" permeation enhancer or combination as used herein means a permeation enhancer or a combination that will provide the desired increase in skin permeability and correspondingly, the desired depth of penetration, rate of administration, and amount of drug delivered.

The phrase "monoalkylether of diethylene glycol" means a chemical having general formula $C_4H_{10}O_3(C_nH_{2n+1})$ wherein n=1-4. Further, the term "glycol" encompasses a broad range of chemicals including but not limited to propylene glycol, dipropylene glycol, butylene glycol, and polyethyleneglycols having general formula $HOCH_2(CH_2OH)_nCH2OH$ wherein n (number of oxyethylene groups)=4-200.

The phrase "thermodynamic activity" of a substance means the energy form involved in skin permeation of this substance. The chemical potential of a substance is defined in thermodynamics as the partial molar free energy of the substance. The difference between the chemical potentials of a drug outside and inside the skin is the energy source for the skin permeation process.

The phrase "permeation enhancer" as used herein means an agent which improves the rate of percutaneous transport of active agents across the skin or use and delivery of active agents to organisms such as animals, whether for local application or systemic delivery.

The phrase "stratum corneum" as used herein means the outer layer of the skin, which comprised approximately 15 layers of terminally differentiated keratinocytes made primarily of the proteinaceous material keratin arranged in a 'brick and mortar' fashion with the mortar being comprised of a lipid matrix made primarily from cholesterol, ceramides and long chain fatty acids. The stratum corneum creates the rate-limiting barrier for diffusion of the active agent across the skin.

The phrase "skin-depot" as used herein means a reservoir or deposit of active agent and dermal penetration enhancer within the stratum corneum, whether it is intra-cellular (within keratinocytes) or inter-cellular.

As stated above, the present invention relates to a transdermal or a transmucosal drug delivery formulation. The invention relates more specifically to a non-occlusive transdermal or transmucosal formulation, preferably in the form of a gel, for use in the delivery of at least one pharmaceutical active ingredient to a warm-blooded animal. Formulations of the present invention may be used for local or systemic delivery.

The formulation may include a permeation enhancer, gelling agent, preservative, antioxidant, buffer, humectant, sequestering agent, moisturizer, surfactant, emollient, or any combination thereof. The active agent may be local anaesthetics; general anaesthetics; muscle relaxant drugs; diuretics; angiotension converting enzyme inhibitors; calcium-channel blockers; anti-arythmics; anti-angina drugs; anti-migraine drugs; antiemetic drugs; anti-histaminic drugs and anti-asthma drugs; thrombolytics; analgesics; antitussive agents; tricyclic antidepressants; amphetamines; anorectics; psychodysleptics; nootropics; hypnotics; analeptics; tricyclic neuroleptics; anti-psychotic drugs; anti-convulsive drugs; hypothalamo-hypophysis regulators; corticosteroids; glucocorticoids; mineralocorticoids; glycemic regulators; hypolipidemia drugs; phosphocalcic metabolism regulators; anti-inflammatory drugs; antisecretive gastric drugs; laxatives; gastric mucosa protectors; gastric motricity modulators; bile salt adsorbants; chelators; gall stone dissolvants; anti-anemia drugs; cutaneous diseases drugs; alpha antagonist drugs; anti-parasitic drugs.

In one embodiment, the pharmaceutical formulation includes testosterone as an active agent and the monoalkyl ether of diethylene glycol and the glycol are in a weight ratio of 1:4. In another embodiment, the active agent is selegilline hydrochloride or fentanyl and the monoalkyl ether of diethylene glycol and glycol are in a weight ratio between about 1:2 to 1:10.

In another aspect of the invention, a method for delaying or inhibiting crystallization of an active agent in a transdermal or transmucosal formulation is provided. It has surprisingly been found that the present invention inhibits or delays for a significant period of time crystallization of the active agent on the skin or mucosal surface. One problem associated with crystallization of the drug on the skin is that the crystals have difficulty crossing the skin or mucosal barrier. Thus, the active agent is left on the skin surface for an extended period of time. As such, there is an increase in the likelihood that the active agent is transferred to clothing or contaminates another being that comes in contact with the user of the pharmaceutical formulation. The present invention by inhibiting or delaying crystallization of the active agent has at least three advantage. The delay or inhibition of the active agent will increase absorption of the drug across the skin or mucosal barrier. Accordingly, there is a minimization of transfer of the pharmaceutical formulation to clothing. Moreover, there is a minimization of contamination of active agent to others.

In accordance with the present invention, the transdermal or a transmucosal pharmaceutical formulation is a drug delivery formulation comprising an active ingredient and a solvent system. The solvent system of the invention includes a pharmaceutically acceptable monoalkyl ether, a pharmaceutically acceptable glycol, and a mixture of an alcohol and water.

For example, the monoalkyl ether is diethylene glycol monomethyl ether, diethylene glycol monoethyl ether or mixtures thereof. Also for example the glycol is propylene glycol, dipropylene glycol or mixtures thereof. The monoalkyl ether and glycol are present in an amount between about 1% and 30% w/w each, and are present in a ratio ranging from 10:1 to 2:1 or 1:2 to 1:10. In a preferred embodiment the pharmaceutically acceptable monoalkyl ether is diethylene glycol monoethyl ether and the glycol is propylene glycol.

Preferably, the solvent system includes a combination of volatile and non-volatile solvents. Examples of non-volatile solvents include but are not limited to propylene glycol, glycerin, liquid polyethylene glycols, or polyoxyalkylene glycols. Examples of volatile solvents include but are not limited to ethanol, propanol, or isopropanol. Preferably, the volatile solvent is a $C_2$-$C_4$ alcohol. For example, the $C_2$-$C_4$ alcohol is preferably ethanol, isopropanol, or mixtures of thereof. The $C_2$-$C_4$ alcohol is present in an amount between about 5 and 80% w/w, and preferably between 15 and 65%, and more preferably between 20 and 50%.

The active ingredient of the formulation includes but is not limited to a hormone such as nonsteroidal estrogens such as benzestrol, broparoestrol, chlorotrianisene, dienestrol, diethylstilboestrol, diethylstilboestrol dipropionate, dimestrol, fosfestrol, hexoestrol, methallenestril and methestrol, and steroidal estrogens such as colpormon, conjugated estrogenic hormones, equilenin, equilin, estradiol, 17 beta-estradiol, estriol, estrone, ethinyl estradiol, estradiol benzoate, estradiol 17 beta-cypionate, polyestradiol phosphate, mestranol, moxestrol, mytatrienediol, quinestradiol, quinestrol; progestogens such as allylestrenol, anagestone, chlomardinone acetate, delmadinone acetate, demegestone, desogestrel, dimethisterone, drospirenone, dydrogesterone, ethynilestrenol, ethisterone, ethynodiol, ethynodiol diacetate, fluorogestone acetate, gestodene, gestonorone caproate, haloprogesterone, 17-hydroxy-16-methylene-.delta.-progesterone, 17.alpha.-hydroxyprogesterone, 17.alpha.-hydroxygesterone caproate, lynestrenol, medrogestone, medroxyprogesterone, megestrol acetate, melengestrol, norethindrone, norethindrone acetate, norethynodrel, norgesterone, norgestimate, norgestrel, norgestrienone, 19 norprogesterone, norvinisterone, pentagestrone, progesterone, natural progesterone, promegestone, quingestrone, trengestone; androgens such as boldenone, cloxotestosterone, fluoxymesterone, mestanolone, mesteronolone, 17-methyltestosterone, testosterone 17 beta-cypionate, testosterone enanthate, testosterone nicotinate, testosterone phenylacetate, testosterone propionate, 17.alpha.-methyltestosterone 3-cyclopentyl enol ether, norethandrolone, normethandrone, oxandrolone, oxymesterone, oxymetholone, prasterone, stanolone, stanolozol, testosterone, tiomesterone.

Moreover, the active agent may be an anti-hormone. For example, the pharmaceutical active agent may include but is not limited to an estrogen, androgen, or progestogen, an anti estrogen such as tamoxifen, 4-OH tamoxifen, anti progestogens and anti androgens.

Also in accordance with the invention, the pharmaceutical active agent may include anti-gout drugs such as colchicine and derivatives, sulfinpyrazone, probenecid, benzbromarone, allopurinol; local anaesthetics such as benzocaine, procaine, tetracaine, lidocaine, etidocaine, prilocaine, mepivacaine, bupivacaine, butanilicaine, articaine, fomocaine; general anaesthetics such as methohexital, thiamylal, thiopenthal, ketamine, etomidate, propofol, midazolam, flumazenil, droperidol, fentanyl, alfentanil, sufentanil; muscle relaxant drugs such as curare derivatives, hexacarbacholine, dantrolene, tetrazepam, carisoprodol, chlorzoxazone, baclofen, memantine, tizandine; diuretics such as hydrochlorothiazide and derivatives, chlortalidone, indapamide, furosemide, bumetanide, piretanide, azosemide, etozolin, ethacrynic acid, amiloride, triamterene, spironolactone; angiotensin converting enzyme inhibitors such as captopril, enalapril, trandolapril, lisinopril, perindopril, benazepril, cilazepril, fosinopril, moexipril, quinapril, ramipril; calcium-channel blockers such as bepridil, diltiazem, felodipine, flunarizine, isradipine, nicardipine, nitrendipine, nifedipine, nimodipine, verapamil, amlodipine, lacidipine, buflomedil, anti-arythmics such as quinidine, ajmaline, procainamide, disopyramide, propafenone, tocainide, phenytoin, aprindine, mexiletine, flecainide, lorcainide, propafenone, sotalol, amiodarone, verapamil, diltiazem; anti-angina drugs such as nitrate derivatives, molsidomine; anti-migraine drugs such as, pizotifene, oxetorone, methysergide sumatriptan, zolmitriptan, naratriptan, eletriptan, almotriptan, rizatriptan; antiemetic drugs such as chlorphenoxamine, dimenhydramine, meclozine, triethylperazine, triflupromazine, metoclopramide, bromopride, domperidone, granisetron, ondansetron, tropisetron, dolasetron, alosteron, tegaserod; anti-histaminic and anti-asthma drugs such as cromoglycate, nedocromil, tritoqualine, ketotifene, lodoxamide, salbutamol, terbutaline, pirbuterol, salmeterol, formoterol, bambuterol, montelukast, pranlukast, theophylline, ipratropium, oxitropium, beclometasone, dexamethasone, fluticasone, budesonide, flunisolide; thrombolytics such as alteplase and derivatives, streptokinase, urokinase; analgesics such as morphine, codeine, diamorphine, dihydrocodeine, hydromorphone, hydrocodone, oxycodone, oxymorphone, levorphanol, pethidine, levomethadone, fenpipramine, piritramide, clofedanol, pentazocine, buprenorphine, butorphanol, nalbuphine, tilidine, tramadol, nefopam, salicylic acid and derivatives, salsalate, diflunisal, acetaminophen, benorylate, mefenamic acid, flufenamic acid, niflumic acid, metamizole, phenazone, phenylbutyazone, aminophenazone, oxyphenbutazone, azapropazone, indometacin, diclofenac, sulindac, felbinac, ibuprofen, naproxen, fenoprofen, flurbiprofen, ketoprofen, tiaprofenic acid, nabumetone, piroxicam, tenoxicam, meloxicam, antitussive agents such as codeine and derivatives, clobutinol, isoaminile, pentoxyverine, butamirate, oxeladine, pipazetate; tricyclic antidepressants such as imipramine, desipramine, trimipramine, lofepramine, clomipramine, opipramol, amitriptyline, amitriptylinoxide, nortriptyline, dibenzepin, doxepin, melitracen; tetracyclic antidepressants such as maprotiline, mianserin; atypical antidepressants such as fluvoxamine, trazodone, viloxacin, fluoxetine; monoamine oxidase inhibitors such as tranylcipromine; serotonin precursors such as oxitriptan; lithium salts; tranquilizers such as meprobamate, hydroxyzine, chlordiazepoxide, temazepam, flurazepam, lormetazepam, nitrazepam, flunitrazepam, diazepam, prazepam, oxazepam, lorazepam, clonazepam, bromazepam, clotiazepam, alprazolam, triazolam, oxazolam, midazolam, ketazolam, brotizolam, clobazam, clorazepate, buspirone; amphetamines and related compounds such as amfetamine, metamfetamine, fenetylline, methylphenidate, prolintane; anorectics such as cathine, amfepramone, mefenorex, propylhexedrine, fenfluramine; psychodysleptics such as N-dimethyltryptamine, psilocin, psilocybin, bufotenin, lysergide, mescaline, tetrahydrocannabinol; nootropics such as pyritinol, piracetam, meclofenoxate; hypnotics such as carbromal, bromisoval, vinylbital, aprobarbital, secbutabarbital, pentobarbital, cyclobarbital, phenobarbital, glutethimide, methyprylon, methaqualone; analeptics such as doxapram; tricyclic neuroleptics such as chlorpromazine, promazine, triflupromazine, alimemazine, levomepromazine, chlorprothixene, pecazine, thioridazine, perphenazine, trifluoperazine periciazine, perazine, fluphenazine, dixyrazine, clopenthixol, dixyrazine, prothipendyl, thithixene, chlorprothixene, clopenthixol, flupentixol; butyrophenones and diphenylbutylpiperidines neuroleptics such as haloperidol, bromperidol, droperidol, trifluperidol, pipamperone, melperone, benperidol, pimozide, fluspirilene; benzamide neuroleptics such as sulpiride; anti-psychotic drugs such as clozapine, haloperidol, olanzapine, quetiapine, risperidone; anti-convulsive drugs such as carbamazepine, valproic acid and its derivatives, primidone, phenyloin, ethosuximide, trimethadione, sultiame, hypothalamo-hypophysis regulators such as gonadoreline, triptoreline, leuprepreline, busereline, gosereline, nafareline, gonadotrophins, follitropins, danazol, clomifene, quinagoline, bromocriptine, lisuride; anti hypo- and anti hyperthyroidy drugs such as thyreotropin releasing hormone, thyreostimuline hormone, triiodothyronine, thyroxine, tiratricol, benzylthiouracile, clotrimazole, corticosteroids; glucocorticoids and mineralocorticoids; glycemia regulators such as insulin, glipizide, glibenclamide, glibornuride, gliclazide, carbutamide, glimepiride, repaglinide, metformine, acarbose, miglitol, glucagon, diazoxide; hypolipidemia drugs such as orlistat, simvastatine, pravastatine, fluvastatine, atorvastatine, tiadenol, cholestyramine, fenofibrate, ciprofibrate, bezafibrate, gemfibrozil, ursodiol; phosphocalcic metabolism regulators such as ergocalciferol, cholecalciferol calcitriol, alfacalcidol, calcifediol, calcipotriol, tacalcitol; anti-inflammatory drugs such as nabumetone, meloxicam, nimesulide, etodolac, alminoprofene, sulfasalazine, mefasalazine, olsalazine, rofecoxib, celecoxib, valdecoxib, nefopam; antisecretive gastric drugs such as omeprazole, lansoprazole, pantoprazole, rabeprazole, misoprostol; laxatives; gastric mucosa protectors such as cimetidine, famotidine, ranitidine, nizatidine, gastric motricity modulators; bile salts adsorbants; chelators; gall stone dissolvants; anti-anemia drugs; cutaneous diseases drugs; alpha antagonist drugs such as urapidil and derivatives, prazosine and derivatives, nicergoline, moxisylyte, anti parasitic drugs such as albendazole, atovaquone, chloroquine, dehydroemetine, diloxanide, furazolidone, halofantrine, iodoquinol, ivermectin, mebendazole, mefloquine, metronidazole, nifurtimox, primaquine, pyrantel, pyrimethamine, quinine, quinidine, penicillins; cephalosporins; aminosids; polypeptides; sulfamides; diaminopyrimidines; tetracyclins; chloramphenicol; thiamphenicol; macrolides; vancomycin; teicoplanin; rifampicin; fusidic acid; 5-nitro-imidazoles; lincosamides; quinolones; isoniazide, ethambutol; antineoplastic drugs such as chlormethine, chlorambucil, melphalan, cyclophosphamide, ifosfamide, estramustine, carnustine, lomustine, fotemustine, carbazine derivatives, cisplatine and derivatives, thiothepa, daunorubicine and derivatives, mitoxantrone, 5-fluorouracil, capecitabine, cytarabine, gemcitabine, mercaptiopurine azathioprine, fludarabine, thioguanine, pentostatine, cladribine, raltitrexed; anti virus drugs such as zidovudine and derivatives, aciclovir and derivatives, foscarnet, ritonavir and derivatives; antifungus drugs such as nystatine, terbinafine, micanazole, ketoconazole, fluconazole, itraconazole, bifonazole, econazole, omoconazole, sulconazole, tioconazole, isoconazole, fenticonazole, sertaconazole.

The active agent may also be selected from an anti-Parkinson drug, an anti-Alzheimer's drug or an opioid analgesic. For example, the opioid analgesic may be fentanyl.

The term "anti-Parkinson drugs" as used herein means any drug administered to a patient for the treatment of Parkinson's Disease or the symptoms associated with Parkinson's Disease, such as but not limited to trihexyphenidyl, tropatepione, biperiden, procyclidine, benzatropine, orphenadrine, bornaprine, metixene, levodopa, or a pharmaceutically acceptable salt thereof. The anti-Parkinson drug may be in the formulation alone or in combination with a decarboxylase inhibitor such as carbidopa or benserazide, bromocriptine, lisuride, amantadine, or selegiline.

The term "anti-Alzheimer drug" as used herein means any drug administered to a patient for the treatment of Alzheimer's Disease or the symptoms associated with Alzheimer's Disease, such as but not limited to galantamine, rivastigmine, donezepil, tacrine, or memantine, or a pharmaceutically acceptable salt thereof.

Further, the active agent may be an alpha-adrenergic agonists such as budralazine, clonidine, epinephrine, fenoxazoline, naphazoline, phenylephrine, phenylpropanolamine, beta-adrenergic agonists such as formoterol, methoxyphenamine, alpha-adrenergic blockers such as doxazosin, prazosin, terazosin, trimazosin, yohimbine, beta-adrenergic blockers such as abenolol, bisoprolol, carteolol, carvedilol, metoprolol, nadolol, penbutolol, nerve agents for smoking cessation such as nicotine, nicotine citrate and nicotine tartrate, anticholinergic agents; antiepileptic agents; antiparkinson agents; bronchodilators; narcotic antagonists; amides such as butoctamide, diethylbromoacetamide, ibrotamide, isovaleryl diethylamide, niaprazine, tricetamide, trimetozine, zolpidem, zopiclone, guanidine derivatives such as guanethidine; quinazoline derivatives such as alfuzosin; reserpine derivatives such as reserpine, sulfonamide derivatives such as furosemide; others such as minoxidil, doxazosin mesylate, moxonidine, and dihydropyridine derivatives such as nilvadipine, nisoldipine, piperazine; derivatives such as flunarisine; others such as perhexyline; calcium regulator such as calcitonin, clodronic acid, dihydrotachysterol, elcatonin, etidronic acid, ipriflavone, pamidronic acid, parathyroid hormone, teriparatide acetate, or selegilline hydrochloride. However, the present invention could be applied to other groups of pharmaceutical active agents not previously mentioned. It is to be understood that the "active agent" is intended to mean a single active agent or a combination of more than one active agent. The amount of the systemically and/or topically active agent included in the formulation is subject to the degree to which penetration enhancement is achieved.

Also in accordance with the invention, permeation enhancers may be additionally incorporated to the pharmaceutical formulation. Permeation enhancers include but are not limited to sulfoxides such as dimethylsulfoxide and decylmethylsulfoxide; surfactants such as sodium laurate, sodium lauryl sulfate, cetyltrimethylammonium bromide, benzalkonium chloride, poloxamer (231, 182, 184), tween (20, 40, 60, 80) and lecithin; the 1-substituted azacycloheptan-2-ones, particularly 1-n-dodecylcyclazacycloheptan-2-one; fatty alcohols such as lauryl alcohol, myristyl alcohol, oleyl alcohol and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate, amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine, terpenes; alkanones, and organic acids, particularly salicylic acid and salicylates, citric acid and succinic acid. As noted earlier herein, "Percutaneous Penetration Enhancers", eds. Smith et al. (CRC Press, 1995), which is incorporated herein by reference thereto, provides an excellent overview of the field and further information concerning possible secondary enhancers for use in conjunction with the present invention. More permeation enhancer(s) suitable to be used with the present invention may be known by those skilled in the art. The permeation enhancer is present from about 0.1 to about 30.0% w/w depending on the type of compound. Preferably the permeation enhancers are fatty alcohols and fatty acids, and more preferably fatty alcohols. Preferably, the fatty alcohols have the formula the $CH_3(CH_2)_n(CH)_mCH_2OH$ wherein n ranges from (8-m) to (16-m) and m=0-2.

The pharmaceutical formulation of the invention may further include a gelling agent or thickener, e.g. carbomer, carboxyethylene or polyacrylic acid such as carbomer 980 or 940 NF, 981 or 941 NF, 1382 or 1342 NF, 5984 or 934 NF, ETD 2020, 2050, 934P NF, 971P NF, 974P NF and carbomer derivatives; cellulose derivatives such as ethylcellulose, hydroxypropylmethylcellulose (HPMC), ethyl-hydroxyethylcellulose (EHEC), carboxymethylcellulose (CMC), hydroxypropylcellulose (HPC), hydroxyethylcellulose (HEC), etc; natural gums such as arabic, xanthan, guar gums, alginates, etc; polyvinylpyrrolidone derivatives; polyoxyethylene polyoxypropylene copolymers, etc; others like chitosan, polyvinyl alcohols, pectins, veegum grades, and the like. Other suitable gelling agents to apply the present invention include, but are not limited to, carbomers. Alternatively, other gelling agents or viscosant known by those skilled in the art may also be used. The gelling agent or thickener is present from about 0.2 to about 30% w/w depending on the type of polymer, as known by one skilled in the art.

The transdermal or transmucosal pharmaceutical formulation may further include preservatives such as benzalkonium chloride and derivatives, benzoic acid, benzyl alcohol and derivatives, bronopol, parabens, centrimide, chlorhexidine, cresol and derivatives, imidurea, phenol, phenoxyethanol, phenylethyl alcohol, phenylmercuric salts, thimerosal, sorbic acid and derivatives. The preservative is present from about 0.01 to about 10% w/w depending on the type of compound.

The transdermal or transmucosal pharmaceutical formulation may further comprise an antioxidant such as but not limited to tocopherol and derivatives, ascorbic acid and derivatives, butylated hydroxyanisole, butylated hydroxytoluene, fumaric acid, malic acid, propyl gallate, metabisulfates and derivatives. The antioxidant is present from about 0.001 to about 5.0% w/w depending on the type of compound.

Also in accordance with the invention, the formulation may further comprise buffers such as carbonate buffers, citrate buffers, phosphate buffers, acetate buffers, hydrochloric acid, lactic acid, tartaric acid, diethylamine, triethylamine, diisopropylamine, aminomethylamine. Although other buffers as known in the art may be included. The buffer may replace up to 100% of the water amount within the formulation.

In one embodiment, the transdermal or transmucosal pharmaceutical formulation further comprises humectant such as glycerin, propylene, glycol, sorbitol, triacetin. The humectant is present from about 1 to 10% w/w depending on the type of compound.

The present formulation may further comprise sequestering agent such as edetic acid. The sequestering agent is present from about 0.001 to about 5% w/w depending on the type of compound.

Also in accordance with the invention, the formulation includes a moisturizer such as docusate sodium, polyoxyethylene alkyl ethers, polyoxyethylene castor oil derivatives, polyoxyethylene stearates, polyoxyethylene sorbitan fatty acid esters, sodium lauryl sulfate. The moisturizer is present from about 1.0 to about 5% w/w depending on the type of compound.

The formulation may further comprise anionic, nonionic, or cationic surfactants. The surfactant is present from about 0.1 to about 30% w/w depending on the type of compound.

Also in accordance with the present invention, the formulation comprises emollients such as but not limited to cetostearyl alcohol, cetyl esters wax, cholesterol, glycerin, fatty esters of glycerol, isopropyl myristate, isopropyl palmitate, lecithins, light mineral oil, mineral oil, petrolatum, lanolins, and combinations thereof. The emollient is present from about 1.0 to about 30.0% w/w depending on the type of compound.

In another aspect of the present invention a method is provide for delaying or inhibiting crystallization of an active agent in a transdermal or transmucosal pharmaceutical formulation. The method includes preparing a formulation comprising at least one active agent and a solvent system, which includes a pharmaceutically acceptable monoalkyl ether of diethylene glycol and a glycol present in a weight ratio of 10:1 to 2:1 or 1:2 to 1:10. In one embodiment of the method, the monoalkyl ether of diethylene glycol and the glycol are present in an ratio of 10:1 to 2:1. In another embodiment of the method, the monoalkyl ether of diethylene glycol and the glycol are present in an amount of about. 1:2 to 1:10.

Preferably, the monoalkyl ether of diethylene glycol and the glycol in combination are present in an amount of at least 15% and no more than 60% of the formulation.

Advantageously, the method decreases or inhibits crystallization of the active agent such that absorption and permeation through the skin or mucosal surface to which it is applied is facilitated or increased. Preferably, the formulation includes a permeation enhancer to increase permeability of the active agent across a dermal or mucosal surface. For example, the formulation may further include lauryl alcohol or myristyl alcohol in an amount between 0.5 to 2% by weight of the total formulation.

EXAMPLES

The following examples are illustrative, and should not be interpreted as limitations to the invention.

Example 1

A gel containing testosterone 1.00% weight by weight (w/w), diethylene glycol monoethyl ether 5.00% w/w, propylene glycol 6.00% w/w, ethanol 46.28% w/w, purified water 38.11% w/w, carbomer (CARBOPOL™ 980 NF) 1.20% w/w, triethanolamine 0.35% w/w, disodium edetic acid (EDTA) 0.06% w/w, lauryl alcohol 2.00% w/w was prepared by dissolving the active ingredient (if not hydro-soluble) in the ethanol/propylene glycol/diethylene glycol monoethyl ether/lauryl alcohol mixture. The disodium EDTA solution was then added and carbomer thoroughly dispersed in the hydro-alcoholic solution under mechanical stirring at room temperature at a suitable speed ensuring good homogenization of the formulation while avoiding lumps formation and air entrapment. Triethanolamine was finally added under stirring to form the gel.

Example 2

A gel composed by testosterone 1.00% w/w, diethylene glycol monoethyl ether 5.00% w/w, propylene glycol 6.00% w/w, ethanol 46.96% w/w, purified water 38.43% w/w, carbomer (CARBOPOL™ 980 NF) 1.20% w/w, triethanolamine 0.35% w/w, disodium EDTA, 0.06% w/w lauryl alcohol 1.00% w/w was prepared according to the manufacturing technique described in Example 1.

Example 3

A gel composed by testosterone 1.00% w/w, diethylene glycol monoethyl ether 5.00%>w/w, propylene glycol 6.00% w/w, ethanol 47.52% w/w, purified water 38.87% w/w, carbomer (CARBOPOL™ 980 NF) 1.20% w/w, triethanolamine 0.35% w/w, disodium EDTA 0.06% w/w, was prepared according to the manufacturing technique described in Example 1.

Example 4

A gel composed by testosterone 1.00% w/w, propylene glycol 6.00% w/w, ethanol 50.26% w/w, purified water 41.13% w/w, carbomer (CARBOPOL™ 980 NF) 1.20% w/w, triethanolamine 0.35% w/w, disodium EDTA, was prepared according to the manufacturing technique described in Example 1.

Example 5

A gel composed by testosterone 1.00% w/w, diethylene glycol monoethyl ether 5.00% w/w, propylene glycol 15.0% w/w, ethanol 42.56% w/w, purified water 34.82% w/w, carbomer (CARBOPOL™ 980 NF) 1.20% w/w, triethanolamine 0.35% w/w, disodium EDTA 0.06% w/w, was prepared according to the manufacturing technique described in Example 1.

Example 6

A gel composed by testosterone 1.00% w/w, diethylene glycol monoethyl ether 30.0% w/w, propylene glycol 6.00% w/w, ethanol 33.76% w/w, purified water 27.62% w/w, carbomer (CARBOPOL™ 980 NF) 1.20% w/w, triethanolamine 0.35% w/w, disodium EDTA 0.06% W/w, was prepared according to the manufacturing technique described in Example 1.

Example 7

A gel composed by testosterone 1.00% w/w, diethylene glycol monoethyl ether 5.00% w/w, propylene glycol 6.00% w/w, ethanol 47.40% w/w, purified water 38.79% w/w, carbomer (CARBOPOL™ 980 NF) 1.20% w/w, triethanolamine 0.35% w/w, disodium EDTA 0.06% w/w, lauryl alcohol 0.20% w/w, was prepared according to the manufacturing technique described in Example 1.

Example 8

A gel composed by testosterone 1.00% w/w, diethylene glycol monoethyl ether 5.00% w/w, ethanol 50.81% w/w, purified water 38.87% w/w, carbomer (CARBOPOL™ 980 NF) 1.20% w/w, triethanolamine 0.35% w/w, disodium EDTA 0.06% w/w, was prepared according to the manufacturing technique described in Example 1.

Example 9

A gel composed by testosterone 1.00% w/w, diethylene glycol monoethyl ether 5.00% w/w, propylene glycol 30.0% w/w, ethanol 34.31% w/w, purified water 28.07% w/w, carbomer (CARBOPOL™ 980 NF) 1.20% w/w, triethanolamine 0.35% w/w, disodium EDTA 0.06% w/w, was prepared according to the manufacturing technique described in Example 1.

Example 10

A gel composed by testosterone 1.00% w/w, ethanol 53.56% w/w, purified water 43.83% w/w, carbomer (CARBOPOL™ 980 NF) 1.20% w/w, triethanolamine 0.35% w/w, disodium EDTA 0.06% w/w, was prepared according to the manufacturing technique described in Example 1.

Example 11

A gel composed by testosterone 1.00% w/w, diethylene glycol monoethyl ether 15.0% w/w, propylene glycol 6.00% w/w, ethanol 42.00% w/w, purified water 34.39% w/w, carbomer (CARBOPOL™ 980 NF) 1.20% w/w, triethanolamine 0.35% w/w, disodium EDTA 0.06% W/W, was prepared according to the manufacturing technique described in Example 1.

Example 12

A gel composed by minoxidil 2.00% w/w, ethanol 58.50% w/w, purified water 39.00% w/w, hydroxypropylcellulose (KLUCEL™ MF Pharm) 0.50% w/w, % w/w, was prepared by dissolving the active ingredient (if not hydrosoluble) in the ethanol/propylene glycol/diethylene glycol monoethyl ether/lauryl alcohol mixture. Purified water was then added and hydroxypropylcellulose thoroughly dispersed in the hydro-alcoholic solution under mechanical stirring at room temperature at a suitable speed ensuring good homogenization of the formulation while avoiding lumps formation and air entrapment until complete swelling.

Example 13

A gel composed by minoxidil 2.00% w/w, diethylene glycol monoethyl ether 5.00% w/w, propylene glycol 30.0% w/w ethanol 37.50% w/w, purified water 25.00% w/w, hydroxypropylcellulose (KLUCEL™ MF Pharm) 0.50% w/w, was prepared according to the manufacturing technique described in Example 12.

Example 14

A gel composed by minoxidil 2.00% w/w, diethylene glycol monoethyl ether 30.0% w/w, propylene glycol 6.00% w/w ethanol 36.90% w/w, purified water 24.60% w/w, hydroxypropylcellulose (KLUCEL™ MF Pharm) 0.50% w/w, was prepared according to the manufacturing technique described in Example 12.

Example 15

A gel composed by oxybutynin base 2.00% w/w, ethanol 58.50% w/w, purified water 39.00% w/w, hydroxypropylcellulose (KLUCEL™ MF Pharm) 0.50% w/w, was prepared according to the manufacturing technique described in Example 12.

Example 16

A gel composed by oxybutynin base 2.00% w/w, diethylene glycol monoethyl ether 5.00% w/w, propylene glycol 30.0% w/w ethanol 37.50% w/w, purified water 25.00% w/w, hydroxypropylcellulose (KLUCEL™ MF Pharm) 0.50% w/w, was prepared according to the manufacturing technique described in Example 12.

Example 17

A gel composed by oxybutynin base 2.00% w/w, diethylene glycol monoethyl ether 30.0% w/w, propylene glycol 6.00% w/w ethanol 36.90% w/w, purified water 24.60% w/w, hydroxypropylcellulose (KLUCEL™ MF Pharm) 0.50% w/w, was prepared according to the manufacturing technique described in Example 12.

Example 18

A gel composed by estradiol 2.00% w/w, ethanol 58.50% w/w, purified water 39.00% w/w, hydroxypropylcellulose (KLUCEL™ MF Pharm) 0.50% w/w, was prepared according to the manufacturing technique described in Example 12.

Example 19

A gel composed by estradiol 2.00% w/w, diethylene glycol monoethyl ether 5.00% w/w, propylene glycol 30.0% w/w ethanol 37.50% w/w, purified water 25.00% w/w, hydroxypropylcellulose (KLUCEL™ MF Pharm) 0.50% w/w, was prepared according to the manufacturing technique described in Example 12.

Example 20

A gel composed by estradiol 2.00% w/w, diethylene glycol monoethyl ether 30.0% w/w, propylene glycol 6.00% w/w ethanol 36.90% w/w, purified water 24.60% w/w, hydroxypropylcellulose (KLUCEL™ MF Pharm) 0.50% w/w, was prepared according to the manufacturing technique described in Example 12.

Example 21

A gel composed by fentanyl base 3.00% w/w, ethanol 58.00% w/w, purified water 38.60% w/w, hydroxypropylcellulose (KLUCEL™ MF Pharm) 0.50% w/w, was prepared according to the manufacturing technique described in Example 12.

Example 22

A gel composed by fentanyl base 5.00% w/w, diethylene glycol monoethyl ether 5.00% w/w, propylene glycol 30.0% w/w ethanol 36.00% w/w, purified water 23.50% w/w, hydroxypropylcellulose (KLUCEL™ MF Pharm) 0.50% w/w, was prepared according to the manufacturing technique described in Example 12.

Example 23

A gel composed by fentanyl base 2.00% w/w, diethylene glycol monoethyl ether 30.0% w/w, propylene glycol 6.00% w/w ethanol 36.90% w/w, purified water 24.60% w/w, hydroxypropylcellulose (KLUCEL™ MF Pharm) 0.50% w/w, was prepared according to the manufacturing technique described in Example 12.

Example 24

A gel composed by testosterone 1.00% w/w, estradiol 0.10% w/w, ethanol 59.00% w/w, purified water 39.40% w/w, hydroxypropylcellulose (KLUCEL™ MF Pharm) 0.50% w/w, was prepared according to the manufacturing technique described in Example 12.

Example 25

A gel composed by testosterone 1.00% w/w, estradiol 0.10% w/w, diethylene glycol monoethyl ether (TRANSCUTOL™ P) 5.00% w/w, propylene glycol 30.0% w/w ethanol 38.00% w/w, purified water 25.40% w/w, hydroxypropylcellulose (KLUCEL™ MF Pharm) 0.50% w/w, was prepared according to the manufacturing technique described in Example 12.

Example 26

A gel composed by testosterone 1.00% w/w, estradiol 0.10% w/w, diethylene glycol monoethyl ether 30.00% w/w, propylene glycol 6.00% w/w ethanol 37.40% w/w, purified water 25.00% w/w, hydroxypropylcellulose (KLUCEL™ MF Pharm) 0.50% w/w, was prepared according to the manufacturing technique described in Example 12.

Example 27

A gel composed by estradiol 0.06% w/w, diethylene glycol monoethyl ether 5.00% w/w, propylene glycol 6.0% w/w, ethanol 46.28% w/w, purified water 41.05% w/w, carbomer (CARBOPOL™ 980 NF) 1.20% w/w, triethanolamine 0.35% w/w, disodium EDTA 0.06% w/w, lauryl alcohol 2.00% w/w, was prepared according to the manufacturing technique described in Example 1.

Example 28

A gel composed by alprazolam 2.00% w/w, ethanol 58.50% w/w, purified water 39.00% w/w, hydroxypropylcellulose (KLUCEL™ MF Pharm) 0.50% w/w, % w/w, was prepared according to the manufacturing technique described in Example 12.

Example 29

A gel composed by alprazolam 2.00% w/w, diethylene glycol monoethyl ether 5.00% w/w, propylene glycol 30.0% w/w ethanol 37.50% w/w, purified water 25.00% w/w, hydroxypropylcellulose (KLUCEL™ MF Pharm) 0.50% w/w, was prepared according to the manufacturing technique described in Example 12.

Example 30

A gel composed by alprazolam 2.00% w/w, diethylene glycol monoethyl ether 30.0% w/w, propylene glycol 6.00% w/w ethanol 36.90% w/w, purified water 24.60% w/w, hydroxypropylcellulose (KLUCEL™ MF Pharm) 0.50% w/w, was prepared according to the manufacturing technique described in Example 12.

COMPARATIVE EXAMPLES OF-IN VITRO DRUG BIODISTRIBUTION AND PERMEATION STUDIES

Example 31

In vitro drug biodistribution and permeation experiments through ear pig skin were made using the diffusion chamber that is schematically shown in FIG. 1 (Franz Vertical Diffusion Cell). Cutaneous penetration studies in vitro through human skin are limited due to the lack of availability of the human skin. It is largely described in the literature that ear pig skin can be used as the closest model to human skin in the assessment of percutaneous absorption of chemicals.

Fresh cadaver ear pig skin obtained from slaughterhouses was processed according to standard operating procedures. The ears were evaluated on their integrity (no bites, scratches or redness) and condition. The skin was excised from the ears with the help of scalpels, avoiding perforations or any damage. The excised skin samples were rinsed with PBS solution and placed on a surface for successive punching of skin disks. The skin disk pieces were mounted between the sections of a vertical diffusion cell having 1.77 sqcm of surface area, the epidermal facing up. 50 mg of the transdermal devices exemplified previously was applied over the epidermal layer whilst the dermal layer contact with the receptor solution: 2.0% weight by volume polyoxyethylene 20 oleyl ether (Oleth 20), with phosphate buffer solution PBS 10 mM, pH 7.4. The receptor chamber was maintained at 35° C. and the studies were conducted under non-occlusive conditions and at 600 rpm of stirring speed. At given time points, samples were withdrawn from the receptor solution and the receptor chamber was immediately refilled with fresh solution. All samples taken from the receptor solution (permeated drug) were analyzed using a high performance liquid chromatography (HPLC) method. After completion of the permeation study, and utilizing appropriate solvents formulation, all skin disk pieces were analysed in drug distribution within the skin layers: dermis, epidermis and stratum corneum. Unabsorbed formulation was also assessed. Then, balance mass was performed in order to assess total recovery/distribution of drug after certain time following drug product administration/application, considering unabsorbed formulation, the amount of drug in the stratum corneum and the amount of drug within the innermost layers of the skin (epidermis, dermis, and receptor solution representing the bloodstream). The different compartments were analyzed using a high performance liquid chromatography (HPLC) method.

Cumulated Drug Permeated and Drug Flux Determination (In Vitro Permeation Study)

The total amount of drug permeated (mcg/cm2) during the study duration and the transdermal flux (mcg/sqcm/h) were determined for each study.

Biodistribution Study

After completion of the in vitro permeation study, distribution of the active compound was assessed for the different compartments as explained before. In order to demonstrate the improvements in the permeation performance applying the invention herein discloses, as well as improvements in minimizing amount of drug that can potentially being transferred to clothes or partners, in vitro permeation studies and drug biodistribution studies of examples using the inventive means were compared with examples made without using this invention. It was an objective to demonstrate the results obtained applying the invention herein disclose. By carrying out drug biodistribution studies in vitro and though, assessing the amount of drug remaining on the skin surface which can potentially be transmitted or transferred to other surfaces or partners when the formulation is used "in vivo".

Example 32

Comparison Between a Formulation of the Present Invention and a Prior Art Formulation Refer to "Examples" above for the quali-quantitative formulations of the examples cited below.

TABLE I

Testosterone in vitro 24-hour biodistribution
Normalized recovery (% of total relative recovery)

| Compartments | Example 10 (control) | | | Example 9 (TC:PG ratio 1:6) | | | Example 6 (TC:PG ratio 5:1) | | |
|---|---|---|---|---|---|---|---|---|---|
| | Mean % | SD % | N | Mean % | SD % | N | Mean % | SD % | N |
| Unabsorbed formulation | 92.5 | 20.1 | 4 | 66.5 | 32.2 | 4 | 82.4 | 15.9 | 4 |
| Stratum corneum | 5.7 | 3.0 | 4 | 12.6 | 8.3 | 4 | 6.6 | 4.0 | 4 |
| Epidermis | 1.8 | 0.5 | 4 | 20.9 | 4.8 | 4 | 11.1 | 5.5 | 4 |
| Dermis | | | | | | | | | |
| Receptor | | | | | | | | | |
| TOTAL | 100.0 | | | 100.0 | | | 100.0 | | |

Figure 2:
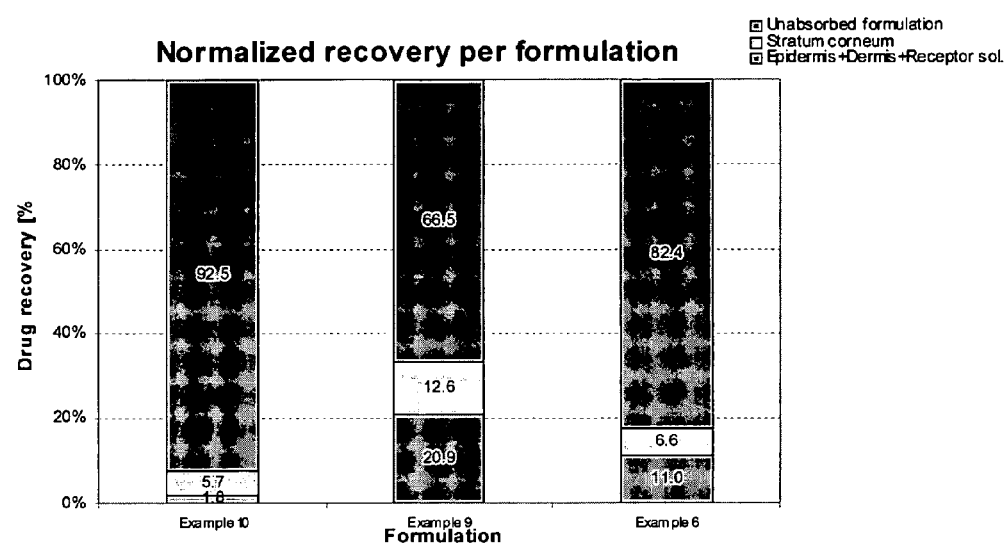
FIG. 2 is a graph illustrating in-vitro 24-hour biodistribution of Testosterone of selected formulation examples disclosed herein.

Table 1 above clearly shows a significant decrease in the amount of drug that is unabsorbed when a transdermal or transmucosal formulation of the present invention is used compared a transdermal or transmucosal formulation that does not include the novel ratio of monoalkyl ester and glycol. As shown, after 24 h, a huge amount of testosterone (92.5%) remained unabsorbed from example 10, which does not include the novelty of the present invention, conversely, examples 9 and 6, both embodiments of the present invention had significantly less unabsorbed drug, 66.5% and 82.4% respectively. FIG. 2 illustrates these results in graphic format.

Table 1 above and FIG. 2 show that a higher amount of testosterone (12.6% versus 6.6%) is present in the stratum corneum in example 9 where the invention is present in a ratio of 1:6 than in example 6 where the invention is present in a ratio of 5:1. This result shows that accumulation of active drug in the outermost layer of the skin or the mucosa does result from the combination of diethylene glycol monoethyl ether:propylene glycol in defined ratios, and does not only depend on diethylene glycol monoethyl ether concentration as expected by the background described previously.

This biodistribution study demonstrates the usefulness of the present invention (i.e. a combination of diethylene glycol monoethyl ether and propylene glycol tested in this case at two extreme ratios: 1:6 and 5:1) and that the present invention significantly reduces formulation skin residues.

TABLE II

Minoxidil 24-hour biodistribution
Normalized recovery (% of total relative recovery)

| Compartments | Example 12 (control) | | | Example 13 (TC:PG ratio 1:6) | | | Example 14 (TC:PG ratio 5:1) | | |
|---|---|---|---|---|---|---|---|---|---|
| | Mean % | SD % | N | Mean % | SD % | N | Mean % | SD % | N |
| Unabsorbed formulation | 95.5 | 2.7 | 4 | 84.4 | 9.3 | 4 | 92.8 | 4.9 | 4 |
| Stratum corneum | 3.1 | 1.6 | 4 | 6.1 | 1.5 | 4 | 2.1 | 1.5 | 4 |
| Epidermis | 1.5 | 0.2 | 4 | 9.5 | 5.1 | 4 | 5.1 | 2.8 | 4 |
| Dermis | | | | | | | | | |
| Receptor | | | | | | | | | |
| TOTAL | 100.0 | | | 100.0 | | | 100.0 | | |

Figure 3:
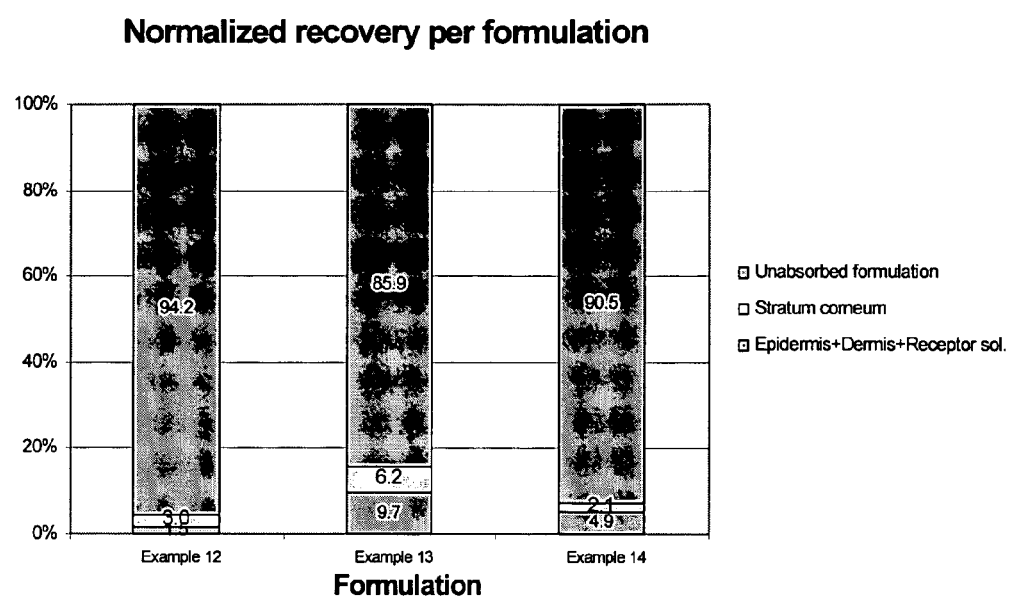
FIG. 3 is a graph illustrating in-vitro 24-hour biodistribution of Minoxidil of selected formulation examples disclosed herein.

Table II illustrates the results of a 24-hour biodistribution study using Minoxidil as the active agent. The results clearly confirm a significant decrease in the amount of drug unabsorbed when the invention is present in the formulation. As shown in Table II and also in FIG. 3 (in graphic form), after 24 h, 94.2% of minoxidil remained unabsorbed from example 12, but examples 14 and more particularly example 13 both of which are preferred embodiments of the present invention, more minoxidil was absorbed. Specifically, example 14 had 90.5% of unabsorbed drug, and example 13 had 85.9%. Table II and FIG. 3 also show a higher amount of minoxidil (6.2% versus 2.1%) was present in the stratum corneum in example 13, wherein the monoalkyl ether and the glycol are present in a ratio of 1:6, and example 14 where the monoalkyl ether and the glycol are present in a ratio of 5:1. Thus, again it is shown that accumulation of active drug in the outermost layer of the skin or the mucosa does result from the synergistic combination of diethylene glycol monoethyl ether:propylene glycol in defined ratios, in which crystallization is inhibited. As shown herein, crystallization inhibition does not only depend on diethylene glycol monoethyl ether concentration as expected by the background described previously, but on the specified ratios of the present invention.

Therefore, these in vitro permeation and biodistribution studies demonstrate the unexpected results of the a combination of diethylene glycol monoethyl ether:propylene glycol tested in this case at two extreme ratios: 1:6 and 5:1, which significantly reduces formulation skin residues.

Example 33

Comparison Between Formulation Containing the Invention Herein Described in Different Ratios Three different formulations, each of which contained a fixed concentration of diethylene glycol monoethyl ether (5% w/w) and a variable concentration of propylene glycol (6, 15 or 30% w/w) were prepared, and compared in a drug permeation and a drug biodistribution after 24 hours; Examples, 3, 5, and 9 above. The results of the permeation study are found in Table III below.

TABLE III

Testosterone 24-hour in vitro permeation

| | Testosterone Cumulative Amount - 24 hours ($\mu g/cm^2$) Mean ± SD | | |
|---|---|---|---|
| Time (h) | Example 3 | Example 5 | Example 9 |
| 0 | 0 | 0 | 0 |
| 6 | 3.9 ± 3.1 | 2.1 ± 1.7 | 1.5 ± 1.0 |
| 12 | 10.9 ± 6.1 | 9.9 ± 8.3 | 7.2 ± 5.6 |
| 18 | 16.9 ± 6.5 | 21.4 ± 13.4 | 18.1 ± 12.0 |
| 24 | 20.7 ± 6.7 | 31.0 ± 14.5 | 29.5 ± 14.6 |

Figure 4:
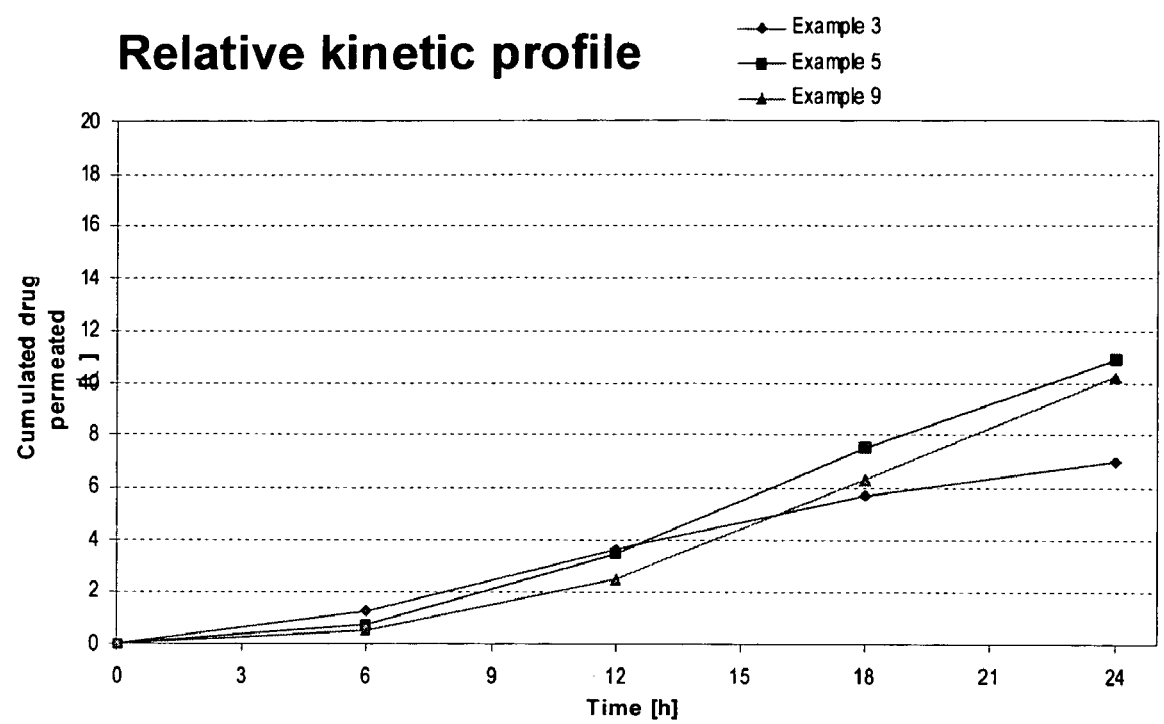
FIG. 4 is a kinetic profile of in-vitro permeation of Testosterone of selected formulation examples disclosed herein.

Table III shows that three different embodiments of the present invention, each of which have different ratios ranging from 1:1.2 to 1:6 of diethylene glycol monoethyl ether:propylene glycol, result in significantly similar cumulated amounts of permeated testosterone. FIG. 4 illustrates the relative kinetic profile of each of these three embodiments of the present invention.

Changes in the quantitative formulation of the present invention do not result in any significant permeation variation.

TABLE IV

Testosterone 24-hour biodistribution
Normalized recovery (% of total relative recovery)

| | Example 3 (control) | | | Example 5 (TC:PG ratio 1:6) | | | Example 9 (TC:PG ratio 5:1) | | |
|---|---|---|---|---|---|---|---|---|---|
| Compartments | Mean % | SD % | N | Mean % | SD % | N | Mean % | SD % | N |
| Unabsorbed formulation | 88.6 | 4.1 | 4 | 79.0 | 18.5 | 4 | 75.1 | 16.0 | 4 |
| Stratum corneum | 2.6 | 1.5 | 4 | 4.8 | 2.2 | 4 | 8.1 | 3.1 | 4 |
| Epidermis | 8.8 | 2.3 | 4 | 16.2 | 4.8 | 4 | 16.8 | 3.5 | 4 |
| Dermis | | | | | | | | | |
| Receptor | | | | | | | | | |
| TOTAL | 100.0 | | | 100.0 | | | 100.0 | | |

Figure 5:
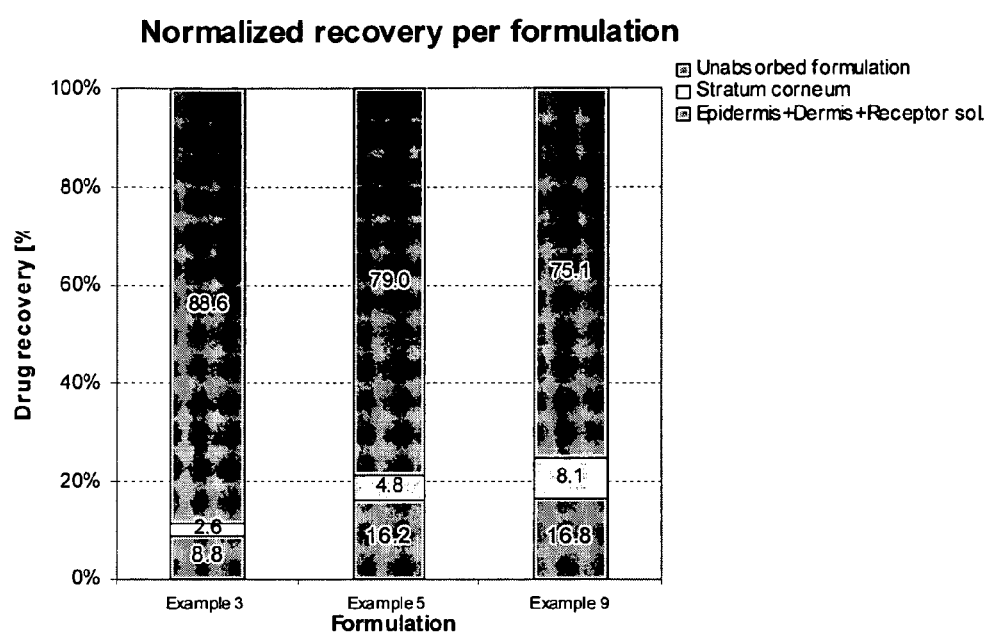
FIG. 5 is a graph illustrating in vitro 24 hour biodistribution of Testosterone of the formulation examples shown in FIG. 4.

As shown in Table IV above, and in FIG. 5, increasing the ratio of the present formulation from 1:3 (5% w/w diethylene glycol monoethyl ether/15% w/w propylene glycol) in example 5 to 1:6 in example 9 (5% w/w diethylene glycol monoethyl ether/30% w/w propylene glycol) only resulted in a 5% decrease of unabsorbed drug, but resulted in a about 66% increase of drug distributed in the stratum corneum. Drug distributed deeper in the skin layers can be considered as unchanged. This study demonstrates that it is possible to modify the distribution of the active drug within the outermost layers of the skin or the mucosa while simultaneously not affecting significantly drug distribution in the innermost layers of the skin or the mucosa (example 5 and 9).

This set of in vitro permeation and biodistribution studies clearly demonstrate that drug distribution is modulated by the ratio of the formulation of the present invention. These in vitro permeation and biodistribution studies also clearly demonstrate that changes of the ratio in which the novel formulation of the present invention do not result in significantly different permeation performances. Additionally, these in vitro permeation and biodistribution studies clearly demonstrate that the novel formulation of the present invention has an independent effect.

Example 34

In Vitro Permeation of Selegilline Hydrochloride

Investigations were undertaken to compare the permeation results of one simple hydroalcoholic gel formulation (formulation A) and two gel formulations containing the present invention (formulations B and C). All three formulations comprised selegilline HCl in 1% ww (corresponding to 0.84% w/w selegilline base).

The components of each of Formulations A, B, and C, are represented below.

| Formulation | A % w/w | B % w/w | C % w/w |
|---|---|---|---|
| Selegilline HCl | 1.00 | 1.00 | 1.00 |
| Diethylene glycol ethyl ether (Transcutol P) | — | 5.00 | 5.00 |
| Propylene glycol | — | 10.0 | 10.0 |
| Lauryl alcohol | — | — | 1.00 |
| Hydroxypropyl cellulose (Klucel HF) | 1.50 | 1.50 | 1.50 |
| Ethanol | 40.0 | 40.00 | 40.0 |
| Triethanolamine | | q.s. pH 6.5 | |

The following conditions and parameters were used for the in-vitro permeation of selegilline hydrochloride examples A, B, and C, described above.

Figure 7:
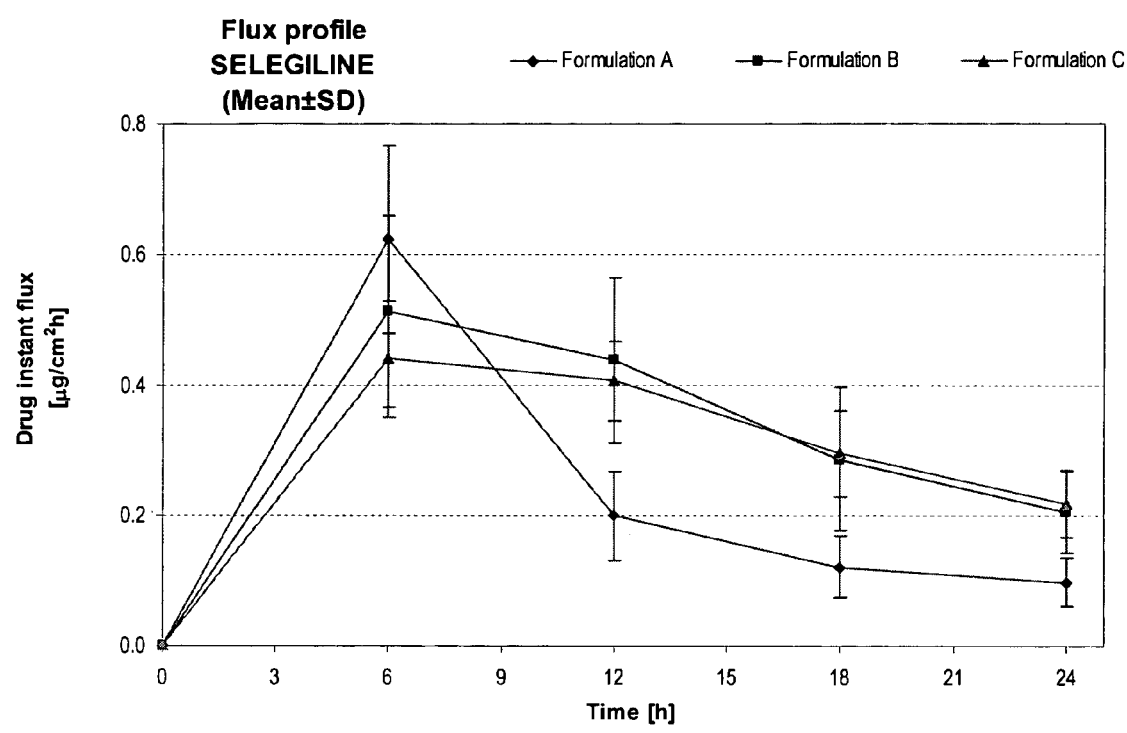
FIG. 7 is a comparative drug flux of selegilline formulations comprising the present invention compared to other formulations.

The data obtained in this Study illustrates the beneficial effect of the diethylene glycol ethyl ether and propylene glycol in a 1:2 ratio and present in an amount of 15% of the total formulation. As shown in FIG. 7, the percentage of cumulated drug permeated is greater for the formulations comprising the present invention. In addition, as shown in FIG. 6, a maximum drug instant flux is attained after 6 hours for both Formulation A, which does not comprise the present invention, and Formulation B, which contains the present invention. However, the drug flux drops 4.5 times quicker for Formulation A as compared to Formulation B within 6 hours. The drug instant flux decreases by 68% for Formulation A, and by 15% for Formulation B, between T=6 and T=12 hours. Thus, the drug instant flux between T=6 hours and T=12 hours is 2.2 times higher for Formulation B (0.31 ug/cm2 h) than for Formulation A (0.14 ug/cm2/h). The slower depletion of the active agent from Formulation B illustrates a better sustained-release of active agent over time, which would be a benefit for long-term treatment drugs. Advantageously, formulations of the present invention and use of the same may require less frequent administration and may avoid unwanted blood level variations, such as the plasmatic peaks and valleys responsible for undesired adverse effects, and decreased therapeutic efficacy.

Example 35

In Vitro Permeation of Fentanyl

Investigations were undertaken to compare the permeation results of one simple hydroalcoholic gel formulation (formulation A) and two gel formulations containing the present invention (formulations B and C). All three formulations comprised fentanyl in 1% w/w. The components of each of Formulations A, B, and C, are represented below.

| Formulation | A % w/w | B % w/w | C % w/w |
|---|---|---|---|
| Fentanyl base | 1.00 | 1.00 | 1.00 |
| Lauryl alcohol | — | 1.00 | 1.00 |
| Diethylene glycol ethyl ether (Transcutol P) | — | 5.00 | 5.00 |
| Propylene glycol | — | — | 10.00 |
| Hydroxypropyl cellulose (Klucel HF) | 1.50 | 1.50 | 1.50 |
| Ethanol | 40.00 | 40.00 | 40.00 |
| Water | 57.50 | 51.50 | 41.50 |

The data obtained in this Study illustrates the beneficial effect of the diethylene glycol ethyl ether and propylene glycol in a 1:2 ratio and present in an amount of 15% of the total formulation.

Figure 8:
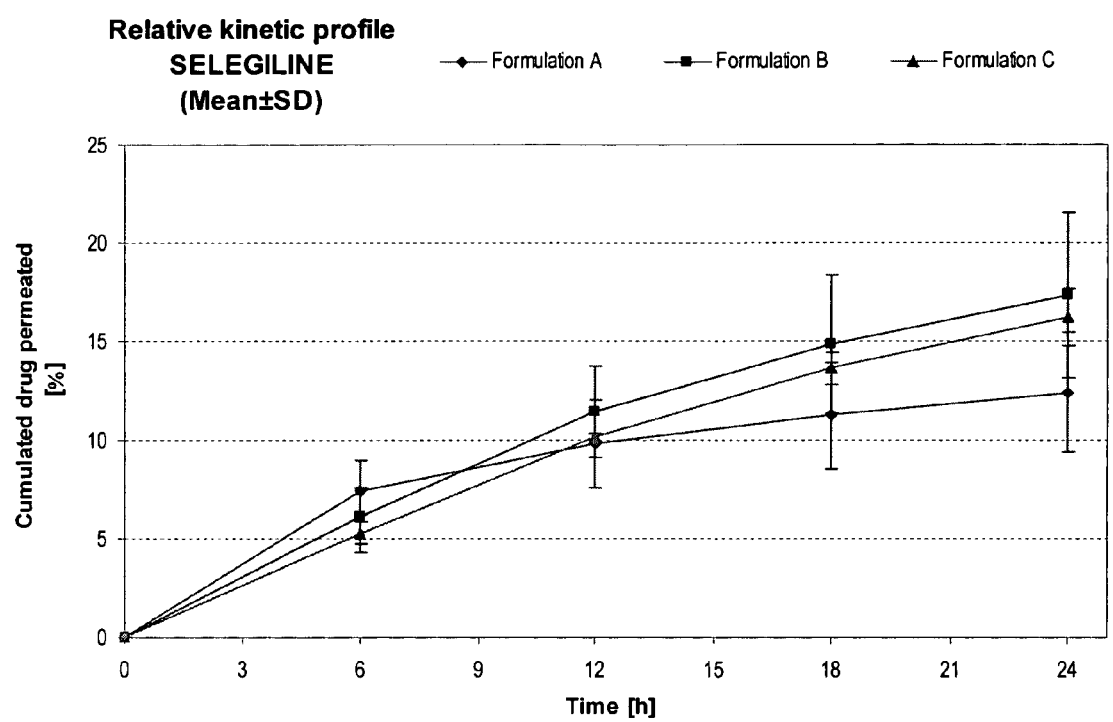
FIG. 8 is an absolute kinetic profile of selegilline formulations comprising the present invention with other formulations.
Figure 9:
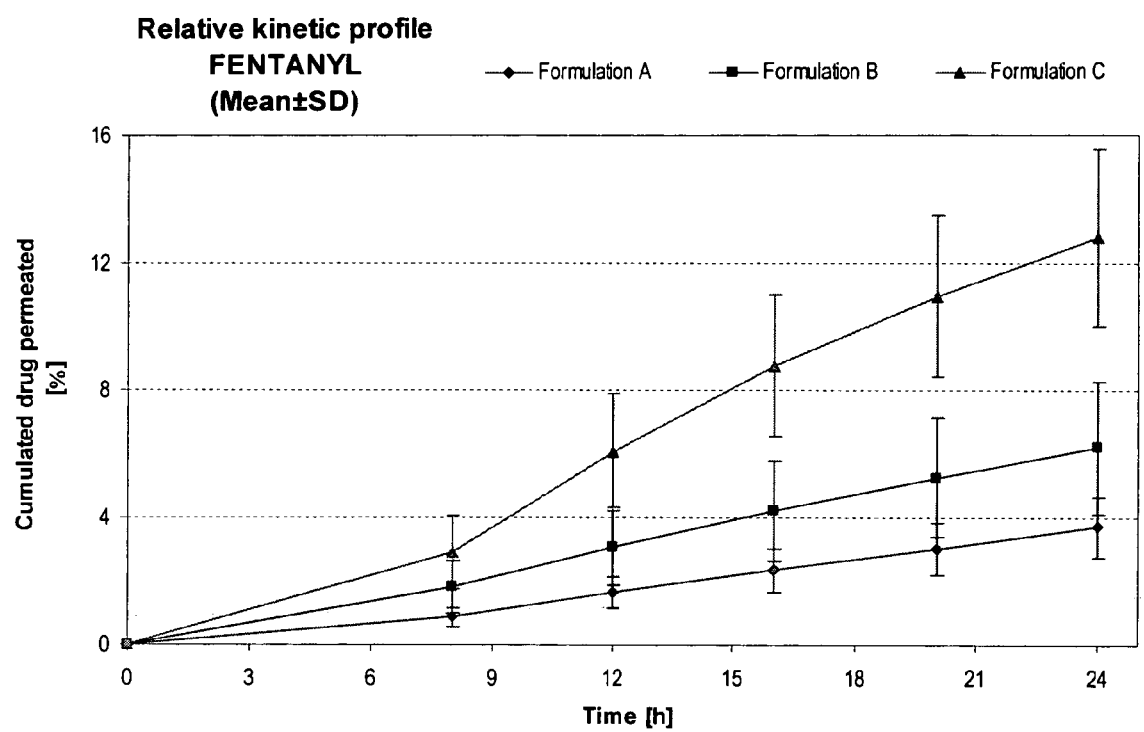
FIG. 9 is an absolute kinetic profile of fentanyl formulations comprising the present invention compared to other formulations.

As shown in FIGS. 8 and 9, the addition of a diethylene glycol ethyl ether 5% and lauryl alcohol % w/w leads to an increase of 76% of the absolute permeated amount of fentanyl, of 68% of the relative permeated amount of fentanyl, and of 55% of the steady-state flux for fentanyl. Thus, the data show that in combination, diethylene glycol ethyl ether and lauryl alcohol have a positive effect on the transdermal absorption of fentanyl.

Further the addition of propylene glycol in an amount of 10% w/w leads to a two-fold increase of the absolute and relative permeated amounts of fentanyl, as well as steady-state flux. Despite the lipophilic feature of fentanyl (LogKo/w=4.05), the addition of a combination of diethylene glycol ethyl ether, lauryl alcohol, and propylene glycol to a simple hydroalcoholic gel has a significant positive effect on drug systemic absorption and to increase three-fold the steady-state flux.

Example 36

In Vitro Permeation of Fentanyl

Investigations were undertaken to compare the permeation results of one simple hydroalcoholic gel formulation (formulation A, same as formulation A disclosed in previous Example 35) and two gel formulations containing the present invention (formulations B and C) in different ratios and in absence of a further permeation enhancer (for instance lauryl alcohol, as in disclosed in previous Example 35). All three formulations comprised fentanyl in 1% w/w. The components of each of Formulations A, B, and C, are represented below.

| Formulation | A % w/w | B % w/w | C % w/w |
|---|---|---|---|
| Fentanyl base | 1.00 | 1.00 | 1.00 |
| Diethylene glycol ethyl ether (Transcutol P) | — | 5.00 | 2.50 |
| Propylene glycol | — | 20.00 | 20.00 |
| Hydroxypropyl cellulose (Klucel HF) | 1.50 | 1.50 | 1.50 |
| Ethanol | 40.00 | 40.00 | 40.00 |
| Water | 57.50 | 32.50 | 35.00 |

The data obtained in this Study illustrates the beneficial effect of the diethylene glycol ethyl ether and propylene glycol in a 1:4 or 1:8 ratio and present in an amount of about 25% of the total formulation.

Figure 10:
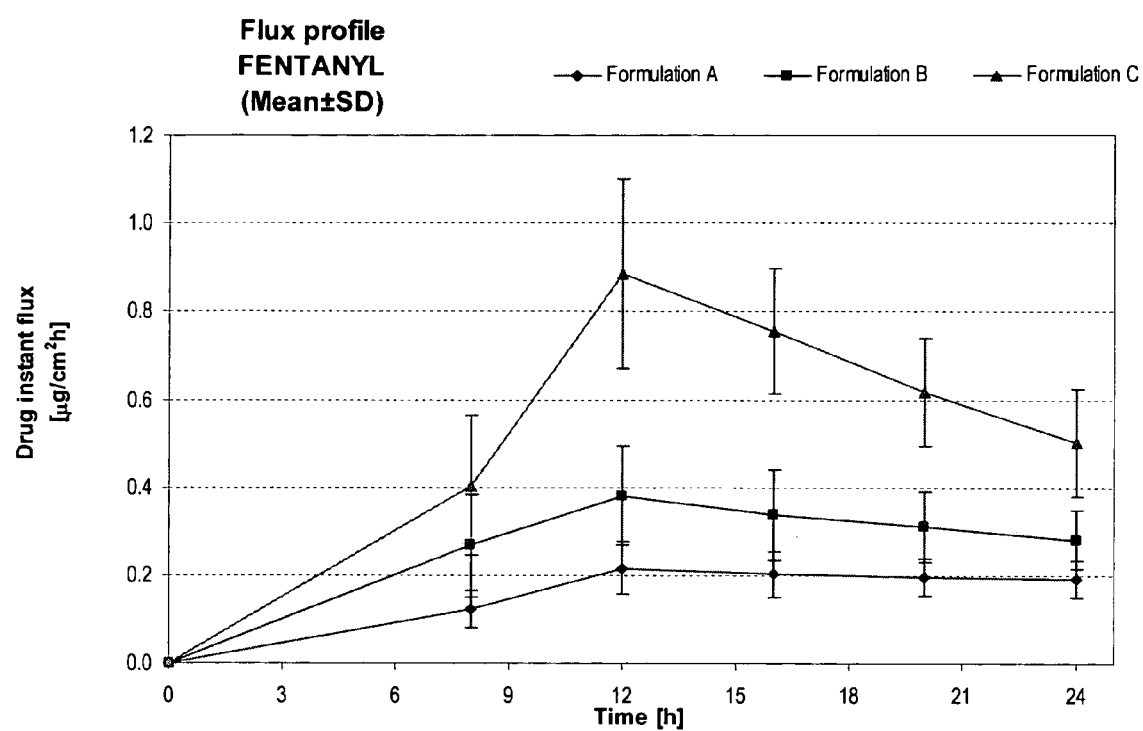
FIG. 10 is a drug flux profile of fentanyl formulations comprising the present invention with other formulations.
Figure 11:
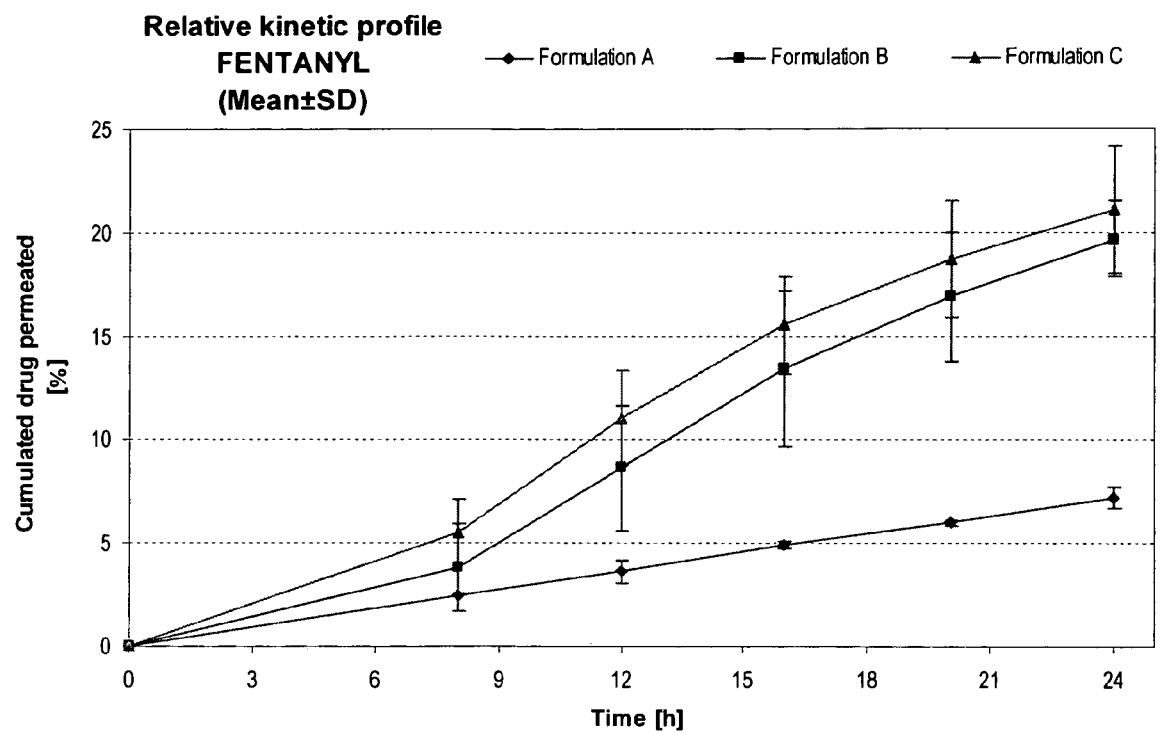
FIG. 11 is an absolute kinetic profile of fentanyl formulations comprising the present invention compared to other formulations.

As shown in FIGS. 10 and 11, the addition of the invention in a ratio of diethylene glycol monoethyl ether: propylene glycol 1:4 (respectively 1:8) in a simple hydroalcoholic gel of fentanyl 1% w/w statistically increases the transdermal absorption of the drug by, respectively, 2.8-fold (respectively, 3.0-fold). Furthermore, this addition allows to reach the steady-state 4 h sooner (at 12 h instead of 16 h) and to significantly increase the steady-state flux value: at the steady-state, the absorption rate is, respectively, 3.3-fold and 3.0-fold higher for B and C than for A. The addition of a combination of diethylene glycol ethyl ether and propylene glycol to a simple hydroalcoholic gel has a significant positive effect on fentanyl systemic absorption.

Example 37

In Vitro Permeation of Buspirone

Investigations were undertaken to compare the permeation results of one simple hydroalcholic gel formulation (formulation A) and two gel formulations containing the present invention (formulations B and C) in different ratios, and in absence or in presence of a further permeation enhancer (myristyl alcohol). All three formulations comprised buspirone hydrochloride in 3% w/w corresponding to 2.74% w/w buspirone base. The components of each of Formulations A, B, and C, are represented below.

| Formulation | A % w/w | B % w/w | C % w/w |
|---|---|---|---|
| Buspirone hydrochloride | 3.00 | 3.00 | 3.00 |
| Diethylene glycol ethyl ether (Transcutol P) | — | 5.00 | 5.00 |
| Propylene glycol | — | 15.00 | 15.00 |
| Myristyl alcohol | — | — | 1.00 |
| Hydroxypropyl cellulose (Klucel ® HF) | 1.50 | 1.50 | 1.50 |
| Ethanol | 30.00 | 30.00 | 35.00 |
| Water | 65.50 | 45.50 | 39.50 |

The data obtained in this Study illustrates the beneficial effect of the diethylene glycol ethyl ether and propylene glycol in a 1:3 ratio and present in an amount of 20% of the total formulation.

Figure 12:
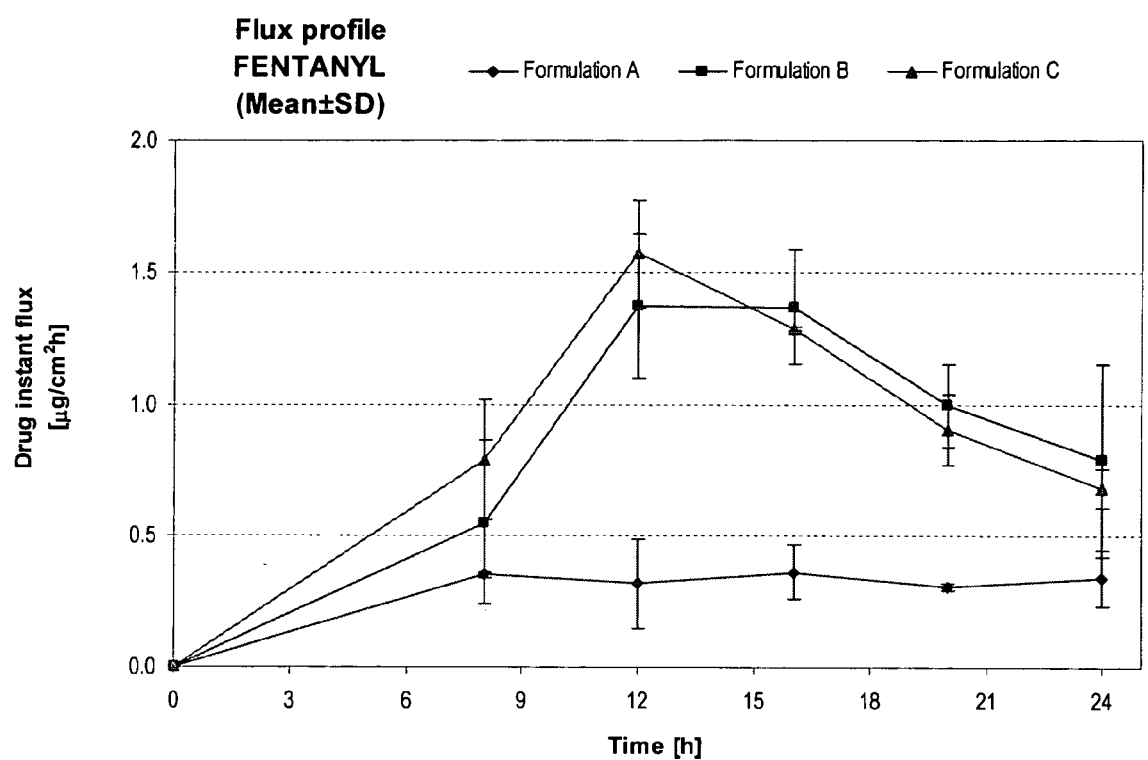
FIG. 12 is a drug flux profile of fentanyl formulations comprising the present invention with other formulations.
Figure 13:
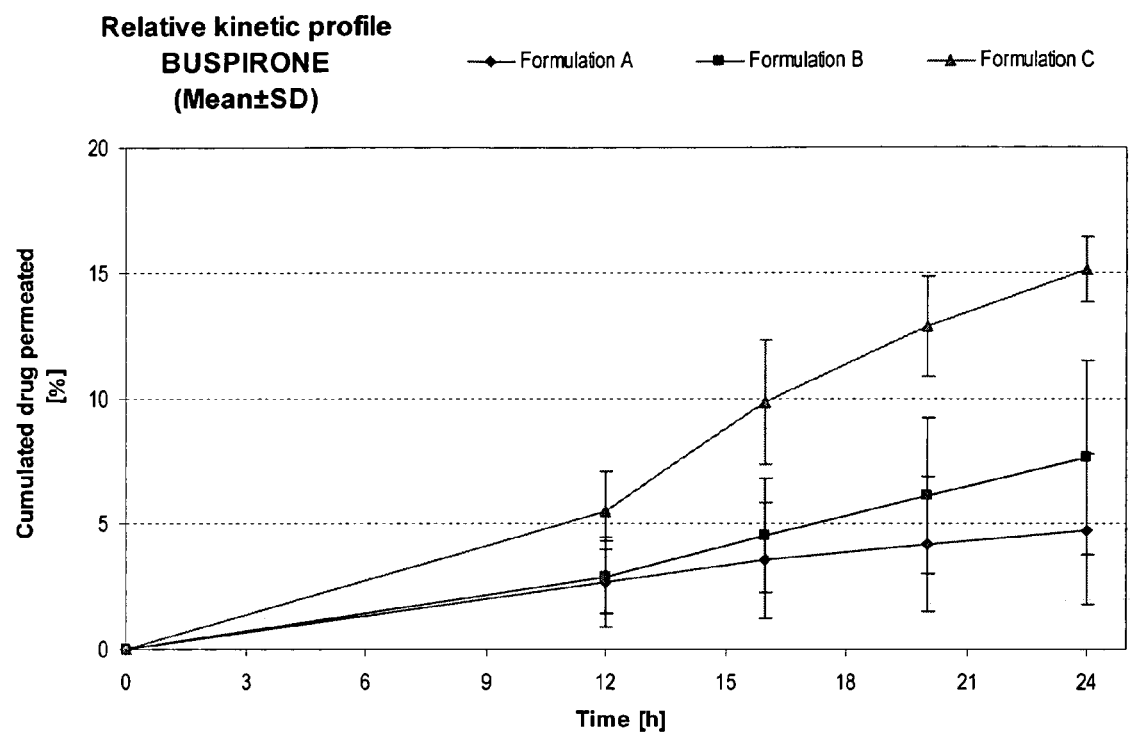
FIG. 13 is an absolute kinetic profile of buspirone formulations comprising the present invention compared to other formulations.
Figure 14:
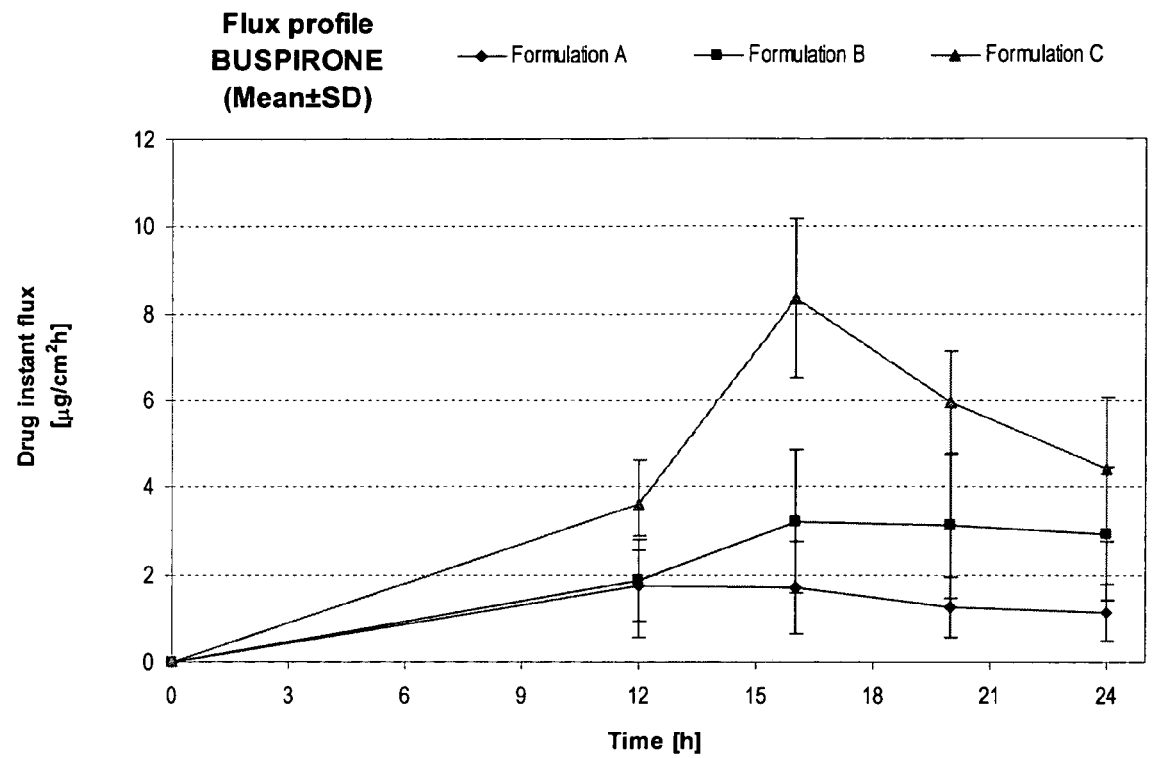
FIG. 14 is a drug flux profile of buspirone formulations comprising the present invention with other formulations.

As shown in FIGS. 12 and 13, the addition of the invention in a ratio of diethylene glycol monoethyl ether: propylene glycol 1:3 (formulation B) in a simple hydroalcoholic gel of buspirone hydrochloride 3% w/w allows to improve the drug absorption by 60% compared to the reference (formulation A). Incorporation of a permeation enhancer—myristyl alcohol—(Formulation C) further improves drug absorption about twice, representing a 3.2-fold increase of buspirone hydrochloride transdermal absorption in comparison with the reference.

The steady-state absorption rate is also improved by 2.2-fold when adding diethylene glycol monoethyl ether:propylene glycol 1:3 (Formulation B versus Formulation A), and by 3.8-fold when further adding myristyl alcohol (Formulation C versus Formulation A).

Example 38

Crystallization Study

Investigations on drug crystallization kinetics were also carried out for the present invention in which the novel formulation of the present invention was compared to formulations not having the novel specified ratio. The objective was to establish a correlation between crystallization kinetics of the novel formulations of the present invention ("slow" or "fast" crystallization rate) with in vitro permeation and biodistribution results, and therefore to determine the partner/surfaces transfer potential of the formulations ("low" or "high" potential).

Different active compounds were evaluated in formulations containing the invention herein disclosed in comparison to formulations without containing the invention. The invention relates to the use of certain combination of vehicles which enhance or promote drug uptake from the skin while minimizing the amounts of skin residual after application of the drug product onto the skin.

Microscopic examination was done on several gel formulations containing the invention herein described and an active compound, compared to formulations which do not contain the invention and the same active compound. Placebo formulations were used for blank comparison as well.

An androgen compound, testosterone (octanol:water partition coefficient, or Log P about 3.3) and minoxidil (Log P about 1.2, thus less lipophilic than testosterone) were used as drug models to exemplify the invention.

An aliquot (1 mL) of the tested formulations was placed on a glass plate and immediately spread with the help of a cover slip to form a homogenous layer of gel. Glass plates holding the sample were, in all cases, let evaporated at controlled room temperature (25° C.) and observations and pictures were made at different times of exposure.

Picture illustrated herein as FIGS. 6a through 6h were taken under the same conditions, i.e., same time points (typically less than 5 minutes; 30 minutes; 2 hours for fast-crystallizing formulations or 4 hours for slow-crystallizing formulations; more than 8 hours in some case), same magnification (total×6.5), same location: the glass plate was positioned once when initiating the study, and then was not further moved until the completion of the study. Some slight differences in contrast and texture are imputable to solvent evaporation.

FIGS. 6a-6h show the crystallization status of some formulations not containing the present invention (Examples 9 and 12) 30 minutes after spreading of the formulations on the glass plate.

Crystallization of Testosterone Formulations

A comparative study focusing on the crystallization rate of testosterone formulations was undertaken in which the rate of crystallization of testosterone formulations of the present invention were compared to other testosterone formulations not comprising the present invention. In this regard, formulations (solutions or semi-solid) were spread over a cover glass and were observed under a microscope for the occurrence of crystal formation.

In the first study, the Gel formulation of Example A was compared to the Gel formulation of Example B for crystallization rate. Example A was ANDROGEL® a 1% testosterone gel marketed in US for male hypogonadism. The ANDROGEL® composition is as follows:

| Ingredient | % w/w |
| --- | --- |
| Testosterone | 1.00 |
| Carbomer C980 NF | 0.90 |
| Isopropyl myristate | 0.50 |
| Ethanol 96% | 71.4 |
| Sodium Hydroxide | 4.72 |
| Purified water | q.s. |

Example A

Composition of ANDROGEL®

Androgel® (Example A), which does not comprise the present invention was compared with Example B, which also does not comprise the present invention. As noted below, Example B is a testosterone gel comprising a diethylene glycol monoethyl ether and propylene glycol in a weight ratio (TC:PG) of 1:1.2. Example A does not comprise either a diethylene glycol monoethyl ether nor propylene glycol.

| Ingredient | % w/w |
| --- | --- |
| Testosterone | 1.00 |
| Carbomer C980 NF | 1.20 |
| Diethylene glycol monoethyl ether (TRANSCUTOL ®, "TC") | 5.00 |
| Propylene glycol ("PG") | 6.00 |
| Disodium edetate | 0.06 |
| Ethanol 96% | 47.5 |
| Triethanolamine | 0.35 |
| Purified water | q.s. |

Results of Example A Compared to Example B.

Crystallization was observed in Example A after 10 minutes of application of the gel formulation to the glass cover. Likewise, crystallization was also observed in Example B in 10 minutes. Thus, no significant difference in the crystallization rate was observed between Example A, ANDROGEL®, and the gel formulation of Example B, which comprises diethylene glycol monoethyl ether and propylene glycol in a 1:1.2 weight ratio.

A comparison study was also undertaken for solution formulations Examples C and D, represented below.

Example C

| Ingredient | % w/w |
| --- | --- |
| Testosterone | 1.00 |
| Isopropyl myristate | 0.50 |
| Ethanol 96% | 71.4 |
| Purified water | q.s. |

Example D

| Ingredient | % w/w |
| --- | --- |
| Testosterone | 1.00 |
| Diethylene glycol monoethyl ether (TRANSCUTOL ®, "TC") | 5.00 |
| Propylene glycol ("PG") | 6.00 |
| Disodium edetate | 0.06 |
| Ethanol 96% | 47.5 |
| Purified water | q.s. |

Crystallization was observed in Example C after only one minute, and in Example D after four minutes. Thus, formulations containing diethylene glycol monoethyl ether and propylene glycol in a 1:1.2 weight ratio do not differ significantly from reference example A, either as a gel formulation or as a solution formulation. A third comparative study was undertaken in which the propylene glycol was increased from 6.00% ww to 20% ww in Examples E and F. (The viscosity was adjusted to the ANDROGEL®; about 8000 cP).

EXAMPLE E

| Ingredient | % w/w |
| --- | --- |
| Testosterone | 1.00 |
| Carbomer C980 NF | 0.60 |
| Diethylene glycol monoethyl ether (TRANSCUTOL ®, "TC") | 5.00 |
| Propylene glycol ("PG") | 20.0 |
| Disodium edetate | 0.06 |
| Ethanol 96% | 47.5 |
| Triethanolamine | 0.35 |
| Purified water | q.s. |

EXAMPLE F: Solution

| Ingredient | % w/w |
| --- | --- |
| Testosterone | 1.00 |
| Diethylene glycol monoethyl ether (TRANSCUTOL ®, "TC") | 5.00 |
| Propylene glycol ("PG") | 20.0 |
| Disodium edetate | 0.06 |
| Ethanol 96% | 47.5 |
| Purified water | q.s. |

Crystallization was not observed in Example E after four hours of application of the formulation to a glass cover. Crystallization was observed after 30 minutes in Example F.

Thus, when both the gel formulation and the solution formulation comprise diethylene glycol monoethyl ether and propylene glycol in a ratio of 1:4, the crystallization rate of both formulations were significantly lower compared to other examples tested.

What is claimed is:

1. A transdermal or transmucosal non-occlusive, semi-solid pharmaceutical formulation comprising:
   at least one active agent of an anti-Parkinson drug, an anti-Alzheimer drug, or an analgesic drug; and
   a solvent system present in an amount sufficient to solubilize the at least one active ingredient and characterized in that it includes:
   (i) a pharmaceutically acceptable monoalkyl ether of diethylene glycol present in an amount of between about 1% and 30% by weight of the solvent system;
   (ii) a pharmaceutically acceptable glycol present in an amount of between about 1% and 30% by weight of the solvent system, with the monoalkyl ether of diethylene glycol and glycol being present in a weight ratio of 10:1 to 2:1 or 1:2 to 1:10 and wherein the monoalkyl ether of diethylene glycol and the glycol in combination are present in an amount of at least 15% and no more than 60% of the formulation; and
   (iii) a mixture of a $C_2$ to $C_4$ alcohol and water which mixture is present in an amount of between about 40% and 98% of the solvent system, wherein the $C_2$ to $C_4$ alcohol is present in an amount of about 5% to 80% of the mixture, and the water is present in an amount of about 20% to 95% of the mixture, so that, compared to formulations containing the same components but in different amounts and ratios, the present solvent system (a) inhibits crystallization of the at least one active ingredient on a skin or mucosal surface of a mammal, (b) reduces or prevents transfer of the formulation to clothing or to another being, (c) modulates biodistribution of the at least one active agent within different layers of skin, (d) facilitates absorption of the at least one active agent by a skin or a mucosal surface of a mammal, or (e) provides a combination of one or more of (a) through (d).

2. The pharmaceutical formulation of claim 1, wherein the monoalkyl ether of diethylene glycol and the glycol are present in a weight ratio of 10:1 to 2:1.

3. The pharmaceutical formulation of claim 1, wherein the monoalkyl ether of diethylene glycol and the glycol are present in a weight ratio of 1:2 to 1:10.

4. The pharmaceutical formulation of claim 1, wherein the monoalkyl ether of diethylene glycol is selected from the group consisting of diethylene glycol monomethyl ether, and diethylene glycol monoethyl ether or mixtures thereof.

5. The pharmaceutical formulation of claim 1, wherein the glycol is selected from the group consisting of propylene glycol, dipropylene glycol or mixtures thereof.

6. The pharmaceutical formulation of claim 1, wherein the glycol modulates the capacity of diethylene glycol monoethyl ether to build a skin depot.

7. The pharmaceutical formulation of claim 1, wherein the $C_2$ to $C_4$ alcohol is selected from the group consisting of ethanol, propanol, isopropanol, 1-butanol, 2-butanol, or mixtures thereof.

8. The pharmaceutical formulation of claim 1, further including a permeation enhancer present in an amount sufficient to increase permeability of the active agent across a dermal or mucosal surface of a mammal.

9. A transdermal or transmucosal non-occlusive, semi-solid pharmaceutical formulation, comprising:
   at least one active agent; and
   a solvent system present in an amount sufficient to solubilize the at least one active ingredient and characterized in that it includes:
   (i) a pharmaceutically acceptable monoalkyl ether of diethylene glycol present in an amount of between about 1% and 30% by weight of the solvent system;
   (ii) a pharmaceutically acceptable glycol present in an amount of between about 1% and 30% by weight of the solvent system, with the monoalkyl ether of diethylene glycol and glycol being present in a weight ratio of 10:1 to 2:1 or 1:2 to 1:10 and wherein the monoalkyl ether of diethylene glycol and the glycol in combination are present in an amount of at least 15% and no more than 60% of the formulation; and (iii) a mixture of a $C_2$ to $C_4$ alcohol and water which mixture is present in an amount of between about 40% and 98% of the solvent system, wherein the $C_2$ to $C_4$ alcohol is present in an amount of about 5% to 80% of the mixture, and the water is present in an amount of about 20% to 95% of the mixture, so that, compared to formulations containing the same components but in different amounts and ratios, the present solvent system (a) inhibits crystallization of the at least one active ingredient on a skin or mucosal surface of a mammal, (b) reduces or prevents transfer of the formulation to clothing or to another being, (c) modulates biodistribution of the at least one active agent within different layers of skin, (d) facilitates absorption of the at least one active agent by a skin or a mucosal surface of a mammal, or (e) provides a combination of one or more of (a) through (d);

wherein the formulation further includes lauryl alcohol or myristyl alcohol present in an amount from 0.5 to 2% by weight of the total formulation.

10. The pharmaceutical formulation of claim 1, wherein the at least one active ingredient includes a hormone or an anti-hormone.

11. The pharmaceutical formulation of claim 1, wherein the at least one active agent is an anti-Parkinson drug selected from the group consisting of selegilline, trihexyphenidyl, tropatepione, bipeiden, procyclidine, benzatropine, orphenadrine, bornaprine, metixene, or levodopa, or a pharmaceutically acceptable salt thereof.

12. The pharmaceutical formulation of claim 1, wherein the at least one active agent is an anti-Parkinson in combination with a decarboxylase inhibitor.

13. A transdermal or transmucosal pharmaceutical formulation comprising:

at least one active agent; and a solvent system present in an amount sufficient to solubilize the at least one active ingredient and characterized in that it includes:

(i) a pharmaceutically acceptable monoalkyl ether of diethylene glycol present in an amount of between about 1% and 30% by weight of the solvent system;

(ii) a pharmaceutically acceptable glycol present in an amount of between about 1% and 30% by weight of the solvent system, with the monoalkyl ether of diethylene glycol and glycol being present in a weight ratio of 10:1 to 2:1 or 1:2 to 1:10; and (iii) a mixture of a $C_2$ to $C_4$ alcohol and water which mixture is present in an amount of between about 40% and 98% of the solvent system, wherein the $C_2$ to $C_4$ alcohol is present in an amount of about 5% to 80% of the mixture, and the water is present in an amount of about 20% to 95% of the mixture, so that, compared to formulations containing the same components but in different amounts and ratios, the present solvent system (a) inhibits crystallization of the at least one active ingredient on a skin or mucosal surface of a mammal, (b) reduces or prevents transfer of the formulation to clothing or to another being, (c) modulates biodistribution of the at least one active agent within different layers of skin, (d) facilitates absorption of the at least one active agent by a skin or a mucosal surface of a mammal, or (e) provides a combination of one or more of (a) through (d), wherein the at least one active agent is an anti-Alzheimer drug selected from the group consisting of galantamine, rivastigmine, donezepil, tacrine, or memantine, or a pharmaceutically acceptable salt thereof.

14. The pharmaceutical formulation of claim 1, wherein the analgesic drug is an opioid analgesic, and further wherein the opioid analgesic is fentanyl, alfentanil, sufentanil, or a pharmaceutically acceptable salt thereof.

15. The pharmaceutical formulation of claim 11, wherein the at least one active agent is selegilline or a pharmaceutically acceptable salt thereof, and the monoalkyl ether of diethylene glycol and the glycol are present in a weight ratio of 1:2 to 1:10.

16. The pharmaceutical formulation of claim 14, wherein the at least one active agent is fentanyl or a pharmaceutically acceptable salt thereof, and the monoalkyl ether of diethylene glycol is monoethyl ether of diethylene glycol, the glycol is propylene glycol, present in a weight ratio of 1:2 to 1:10.

17. The pharmaceutical formulation of claim 1, further comprising an agent selected from the group consisting of gelling agents; permeation enhancers, preservatives, antioxidants, buffers, humectants, sequestering agents, moisturizers, surfactants, emollients, and any combination thereof.

18. A method of delaying or inhibiting crystallization of an active agent in a transdermal or transmucosal pharmaceutical formulation according to claim 1, wherein the formulation comprises at least one active agent and a solvent system, the solvent system comprising a pharmaceutically acceptable monoalkyl ether of diethylene glycol and a glycol present in a weight ratio of 10:1 to 2:1 or 1:2 to 1:10 so that, compared to formulations containing the same components but in different amounts and ratios, the present solvent system inhibits crystallization of the at least one active ingredient when applied to the skin or mucosal surface of a mammal.

19. The method of claim 18, wherein the monoalkyl ether of diethylene glycol and the glycol are present in an ratio of 10:1 to 2:1.

20. The method of claim 18, wherein the monoalkyl ether of diethylene glycol and the glycol are present in an amount of about. 1:2 to 1:10.

21. The method of claim 18, wherein the solvent system further comprises a mixture of a $C_2$ to $C_4$ alcohol and water, the mixture present in an amount of between 40% and 98% of the solvent system.

22. The method of claim 18, wherein the $C_2$ to $C_4$ alcohol is present in an amount between 5% and 80% of the mixture, and the water is present in an amount between 20% and 95% of the mixture.

23. The method of claim 18, wherein the decrease or inhibition of crystallization of the active agent is sufficient to facilitate or increase absorption of the active agent across a skin or mucosal surface to which it is applied.

24. The method of claim 18, wherein the monoalkyl ether of diethylene glycol is selected from the group consisting of diethylene glycol monomethyl ether, and diethylene glycol monoethyl ether or mixtures thereof.

25. The method of claim 18, wherein the glycol is selected from the group consisting of propylene glycol, dipropylene glycol or mixtures thereof.

26. The method of claim 18, which further comprises providing a permeation enhancer present in an amount sufficient to increase permeability of the active agent across a dermal or mucosal surface of a mammal.

27. The method of claim 18, wherein the formulation further includes lauryl alcohol or myristyl alcohol present in an amount from 0.5 to 2% by weight of the total formulation.

28. The method of claim 18, wherein the $C_2$ to $C_4$ alcohol is selected from the group consisting of ethanol, propanol, isopropanol, 1-butanol, 2-butanol, or mixtures thereof.

29. The method of claim 18, characterized in that the at least one active ingredient is selected from the group including sympathomimetics, sympatholytics, parasympathomimetics, parasympatholytics, ganglioplegics, myorelaxants, antihypertensives, diuretics, cardiotonics, anti-arythmics, anti-angina drugs, cerebral and peripheric vasodilatators, anti-migraine drugs, anti-histaminic drugs, anti-asthma drugs, thrombolytics, general anaesthetics, anxiolytics, antidepressants, neuroleptics, anti-convulsive drugs, hypothalamo-hypophysis regulators, hypo and hyperthyroidics, corticosteroids, glycemia regulators, hypolipidemia drugs, phosphocalcic metabolism regulators, antipyretics, anti-inflammatory drugs, anti-acids, antisecretive gastric drugs, laxatives, gastric mucosa protectors, gastric motricity modulators, bile salts adsorbants, chelators, gall stone dissolvants, anti-anemia drugs, cutaneous diseases drugs, antiparasit drugs, antibiotics, penicillins, cephalosporins, aminosids, polypeptides, sulfamides, diaminopyrimidines, tetracyclins, chloramphenicol, thiamphenicol, macrolides, vancomycin, teicoplanin, rifampicin, fusidic acid, 5-nitro-imidazoles, lincosamides, quinolones, anticancer drugs, anti virus drugs, and antifungus drugs.

30. The method of claim 18, wherein the at least one active agent is an anti-Parkinson drug selected from the group consisting of selegilline, trihexyphenidyl, tropatepione, bipeiden, procyclidine, benzatropine, orphenadrine, bornaprine, metixene, or levodopa, or a pharmaceutically acceptable salt thereof.

31. The method of claim 18, wherein the at least one active agent is an anti-Parkinson drug in combination with a decarboxylase inhibitor.

32. The method of claim 18, wherein the at least one active agent is an anti-Alzheimer drug selected from the group consisting of galantamine, rivastigmine, donezepil, tacrine, or memantine, or a pharmaceutically acceptable salt thereof.

33. The method of claim 18, wherein the at least one active agent is an analgesic drug or an opioid analgesic, and further wherein the opioid analgesic is fentanyl, alfentanil, sufentanil, or a pharmaceutically acceptable salt thereof.

34. The method of claim 33, wherein the active agent is fentanyl, the monoalkyl ether of diethylene glycol is monoethyl ether of diethylene glycol, the glycol is propylene glycol, present in a weight ratio of 1:2 to 1:10.

35. The method of claim 30, wherein the active agent is selegilline hydrochloride, the monoalkyl ether of diethylene glycol and the glycol are present in a weight ratio of 1:2 to 1:10.

36. The pharmaceutical formulation of claim 1, wherein the active agent is selected from the group consisting of ropinirole, pramipexole, selegilline, pergolide, rivastigmine, ketoprofen, fentanyl, lidocaine, ondansetron, granisetron, clonidine, minoxidil, amlodipine, alprazolam, nicotine, and a pharmaceutically acceptable salt thereof.

37. A method of delaying or inhibiting crystallization of an active agent in a transdermal or transmucosal pharmaceutical formulation according to claim 9, wherein the formulation comprises at least one active agent and a solvent system, the solvent system comprising a pharmaceutically acceptable monoalkyl ether of diethylene glycol and a glycol present in a weight ratio of 10:1 to 2:1 or 1:2 to 1:10 so that, compared to formulations containing the same components but in different amounts and ratios, the present solvent system inhibits crystallization of the at least one active ingredient when applied to the skin or mucosal surface of a mammal.

38. The method of claim 37, wherein the at least one active agent is an anti-Parkinson drug, an anti-Alzheimer drug, or an analgesic drug.

39. The method of claim 37, wherein the at least one active agent is an anti-Parkinson drug selected from the group consisting of selegilline, trihexyphenidyl, tropatepione, bipeiden, procyclidine, benzatropine, orphenadrine, bornaprine, metixene, or levodopa, or a pharmaceutically acceptable salt thereof.

40. The method of claim 37, wherein the at least one active agent is an anti-Parkinson drug in combination with a decarboxylase inhibitor.

41. The method of claim 37, wherein the at least one active agent is an anti-Alzheimer drug selected from the group consisting of galantamine, rivastigmine, donezepil, tacrine, or memantine, or a pharmaceutically acceptable salt thereof.

42. The method of claim 37, wherein the at least one active agent is an analgesic drug or an opioid analgesic, and further wherein the opioid analgesic is fentanyl, alfentanil, sufentanil, or a pharmaceutically acceptable salt thereof.

43. The method of claim 42, wherein the active agent is fentanyl, the monoalkyl ether of diethylene glycol is monoethyl ether of diethylene glycol, the glycol is propylene glycol, present in a weight ratio of 1:2 to 1:10.

44. The method of claim 39, wherein the active agent is selegilline hydrochloride, the monoalkyl ether of diethylene glycol and the glycol are present in a weight ratio of 1:2 to 1:10.

45. The method of claim 37, wherein the active agent is selected from the group consisting of ropinirole, pramipexole, selegilline, pergolide, rivastigmine, ketoprofen, fentanyl, lidocaine, ondansetron, granisetron, clonidine, minoxidil, amlodipine, alprazolam, nicotine, and a pharmaceutically acceptable salt thereof.

* * * * *

UNITED STATES PATENT AND TRADEMARK OFFICE
CERTIFICATE OF CORRECTION

PATENT NO.         : 7,335,379 B2                                      Page 1 of 2
APPLICATION NO. : 11/371042
DATED                : February 26, 2008
INVENTOR(S)      : Carrara et al.

It is certified that error appears in the above-identified patent and that said Letters Patent is hereby corrected as shown below:

Title Page:
Item (56) References Cited, OTHER PUBLICATIONS:
Ralph Lipp et al. reference, after "Lipp", delete "et al.".
Pramila N. Kotiyana et al. reference, change "Kotiyana" to -- Kotiyan --.

Column 7:
Line 47, before "formulations", change "selegilline" to -- selegiline --.
Line 50, before "formulations", change "selegilline" to -- selegiline --.

Column 9:
Line 54, after "the active agent is", change "selegilline" to -- selegiline --.

Column 13:
Line 57, before "hydrochloride", change "selegilline" to -- selegiline --.

Column 24:
Line 17, before "Hydrochloride", change "Selegilline" to -- Selegiline --.
Line 22, before "HC1", change "selegilline" to -- selegiline --.
Line 23, before "base)", change "selegilline" to -- selegiline --.
Line 31, row 1 of the table after the heading row, change "Selegilline" to -- Selegiline--.
Line 40, before "hydrochloride", change "selegilline" to -- selegiline --.

Column 31:
Line 28 (claim 11, line 3), change "selegilline" to -- selegiline --.
Line 29 (claim 11, line 4), change "bipeiden" to -- biperiden --.

Column 32:
Line 8 (claim 15, line 2), change "selegilline" to -- selegiline --.
Line 40 (claim 20, line 3), change "about." to -- about --.

Column 33:
Line 28, change "selegilline" to -- selegiline --.
Line 29, change "bipeiden" to -- biperiden --.
Line 49, change "selegilline" to -- selegiline --.

UNITED STATES PATENT AND TRADEMARK OFFICE
CERTIFICATE OF CORRECTION

PATENT NO.       : 7,335,379 B2
APPLICATION NO.  : 11/371042
DATED            : February 26, 2008
INVENTOR(S)      : Carrara et al.

It is certified that error appears in the above-identified patent and that said Letters Patent is hereby corrected as shown below:

Column 34:
Line 1, change "selegilline" to -- selegiline --.
Line 22, change "selegilline" to -- selegiline --.
Line 23, change "bipeiden" to -- biperiden --.
Line 43, change "selegilline" to -- selegiline --.
Line 48, change "selegilline" to -- selegiline --.

Signed and Sealed this

Seventeenth Day of June, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,335,379 B2 | Page 1 of 1 |
| APPLICATION NO. | : 11/371042 | |
| DATED | : February 26, 2008 | |
| INVENTOR(S) | : Carrara et al. | |

It is certified that error appears in the above-identified patent and that said Letters Patent is hereby corrected as shown below:

<u>Column 33</u>:
Delete lines 4-25 (claim 29).

Signed and Sealed this

Eighth Day of December, 2009

David J. Kappos
*Director of the United States Patent and Trademark Office*